United States Patent
Sugumi et al.

[19]

[11] Patent Number: 5,952,335

[45] Date of Patent: Sep. 14, 1999

[54] FUSED POLYCYCLIC HETEROCYCLE DERIVATIVES

[75] Inventors: Hiroyuki Sugumi; Jun Niijima; Yoshihiko Kotake; Toshimi Okada; Jun-ichi Kamata; Kentaro Yoshimatsu; Takeshi Nagasu; Katsuji Nakamura; Toshimitsu Uenaka; Atsumi Yamaguchi, all of Ibaraki; Hiroshi Yoshino, Chiba; Nozomu Koyanagi; Kyosuke Kito, both of Ibaraki, all of Japan

[73] Assignee: Eisai Co., Ltd., Tokyo, Japan

[21] Appl. No.: 08/952,778

[22] PCT Filed: May 31, 1996

[86] PCT No.: PCT/JP96/01487

§ 371 Date: Nov. 26, 1997

§ 102(e) Date: Nov. 26, 1997

[87] PCT Pub. No.: WO96/38446

PCT Pub. Date: Dec. 5, 1996

[30] Foreign Application Priority Data

May 31, 1995 [JP] Japan .................. 7-133992
Nov. 28, 1995 [JP] Japan .................. 7-309195

[51] Int. Cl.[6] .............. A61K 31/505; C07D 265/34; C07D 239/70; C07D 279/14

[52] U.S. Cl. .............. 514/274; 514/215; 514/224.5; 514/229.5; 514/248; 514/250; 540/578; 544/14; 544/99; 544/233; 544/245

[58] Field of Search .................. 514/215, 224.5, 514/229.5, 248, 250, 274; 540/578; 544/14, 99, 233, 245

[56] References Cited

U.S. PATENT DOCUMENTS 3,962,438  6/1976  Berkoff et al. .................. 424/247

OTHER PUBLICATIONS

Antonini et al., Synthesis of (Dialkyamino)alkyl–Disubstituted Pyrimido(5,6,1–de) acridines, a Novel Group of Anticancer Agents Active on a Multidrug Resistant Cell Line, J. Med. Chem., vol. 38, No. 17, pp. 3282–3286, 1995.

*Primary Examiner*—Richard L. Raymond
*Assistant Examiner*—Brenda Coleman
*Attorney, Agent, or Firm*—Birch, Stewart, Kolasch & Birch, LLP

[57] ABSTRACT

Novel fused polycyclic heterocycle derivatives having excellent antitumor effects and a process for producing the same. A compound represented by the following general formula (I) or pharmacologically acceptable salts thereof:

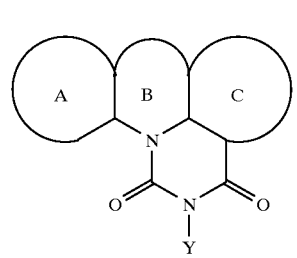

(I)

wherein the ring A represents an optionally substituted monocyclic aromatic ring or a dicyclic fused ring in which at least one of the rings is an aromatic ring; the ring B represents pyrrole, 4H-1,4-oxazine, 4H-1,4-thiazine or 4(1H)-pyridone; the ring C represents an optionally substituted, monocyclic or dicyclic fused aromatic ring; and Y represents a group represented by the formula —e—f (wherein e represents a lower alkylene; and f represents amidino, guanidino or amino optionally substituted by optionally hydroxylated or optionally lower-alkylaminated lower alkyl;

provided that the cases where the rings A and B are both optionally substituted monocyclic aromatic rings are excluded. Which has an excellent antitumor activity.

12 Claims, No Drawings

FUSED POLYCYCLIC HETEROCYCLE DERIVATIVES

This application is a §371 of PCT/JP96/01487, filed May 31, 1996, the entire contents of which are incorporated herein by reference.

TECHNICAL FIELD

This invention relates to novel fused polycyclic heterocycle derivatives, a process for producing the same and medicinal compositions containing the same as the active ingredient.

BACKGROUND ART

A tricyclic compound amonafide [5-amino-2-[2-(dimethylamino)ethyl]-1H-benz[de]isoquinoline-1,3(2H)-dione] is the most famous fused polycyclic heterocycle antitumor compound having a cyclic imido moiety

in its molecule. However, it is reported that amonafide showed a strong bone marrow toxicity and a poor efficacy in clinical tests carried out hitherto [Drugs Fut., 17, 832 (1992)]. As a tetracyclic compound, there is reported azonafide [2-[2'-(dimethylamino)ethyl]-1,2-dihydro-3H-dibenz(deh)-isoquinoline-1,3-dione] obtained by converting the aminonaphthalene moiety of amonafide into anthracene to thereby enhance the antitumor activity in preclinical tests (WO9200281).

As fused tetracyclic heterocycle antitumor substances having a uracil structure wherein a nitrogen atom has been introduced into a cyclic imido moiety, there have been known 2-[2-(dimethylamino)ethyl]pyrimid[5,6,1-de]acridine-1,3,7-trione [Farmaco, 47, 1035 (1992)] and 2,3-dihydro-2-[2-(dimethylamino)ethyl]-1H,7H-naphthylidino[3,2,1-ij]quinazoline-1,3,7(2H)-trione [J. Med. Chem., 37, 593 (1994)]. However each of these compounds showed only a weak antitumor activity in preclinical tests. There has been reported neither pentacyclic nor hexacyclic fused heterocycle antitumor substances of this type.

The present invention aims at providing novel compounds or novel fused pentacyclic and hexacyclic heterocycle derivatives having low toxicity and excellent antitumor activity. The present invention also aims at providing a process for producing these compounds and medicinal compositions containing as the active ingredient these compounds.

DISCLOSURE OF THE INVENTION

To achieve the above-mentioned objects, the present inventors have conducted extensive studies in order to develop excellent antitumor substances. As a result, they have successfully found out that novel fused pentacyclic and hexacyclic heterocycle compounds having a uracil structure in the molecule have excellent antitumor activity and low toxicity, thus completing the present invention.

That is, the present invention relates to a compound represented by the following general formula (I) or pharmacologically acceptable salts thereof:

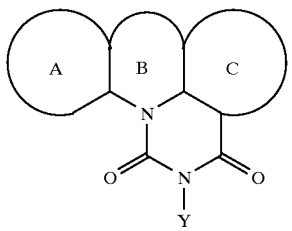

wherein the ring A represents an optionally substituted monocyclic aromatic ring or a dicyclic fused ring in which at least one of the rings is an aromatic ring; the ring B represents pyrrole, 4H-1,4-oxazine, 4H-1,4-thiazine or 4(1H)-pyridone; the ring C represents an optionally substituted, monocyclic or dicyclic fused aromatic ring; and Y represents a group represented by the formula —e—f wherein e represents lower alkylene; and f represents amidino, guanidino or amino, which can be optionally substituted with a lower alkyl which can be optionally hydroxylated or optionally lower-alkylaminated;

provided that the cases where the rings A and C are both optionally substituted monocyclic aromatic rings are excluded.

Further, the present invention relates to a medical composition comprising a fused polycyclic heterocycle as derivative described above in a pharmacologically efficacious dose or pharmacologically acceptable salts thereof and pharmacologically acceptable carriers.

Further, the present invention relates to a method for preventing or treating tumors by administering a fused polycyclic heterocycle derivative as described above in a pharmacologically efficacious dose to a patient.

In the definition of the ring A in the above general formula (I), the term "monocyclic aromatic ring" means an aromatic 5- or 6-membered ring optionally containing at least one oxygen or sulfur atom. The term "dicyclic fused ring in which at least one of the rings is an aromatic ring" means a dicyclic fused ring in which each of the rings is a 5- to 8-membered ring optionally containing at least one nitrogen, oxygen or sulfur atom and at least one of the rings is an aromatic ring. It may have one to three substituents on the rings.

Examples of the ring A include benzene, pyridine, pyrazine, pyrimidine, pyridazine, furan, thiophene, pyrrole, thiazole and the following dicyclic fused rings which may be partly hydrogenated and oxidized at a sulfur atom, if contained therein. These rings may be fused to the ring B at an arbitrary position allowable chemically.

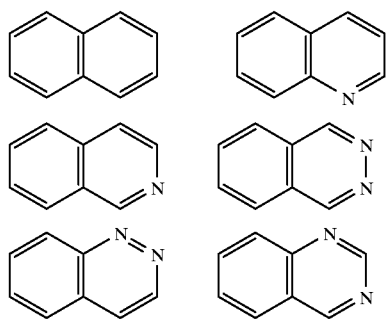

-continued
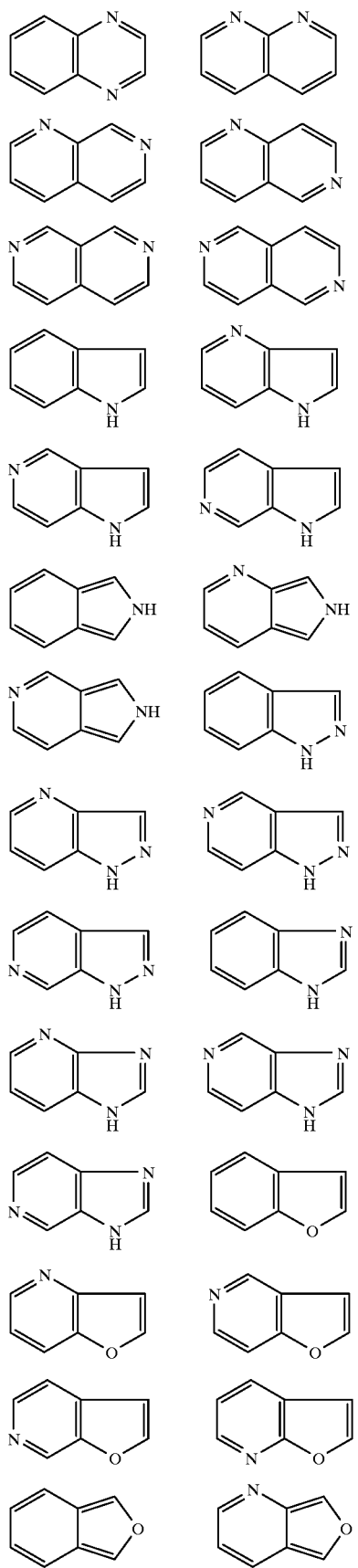
-continued
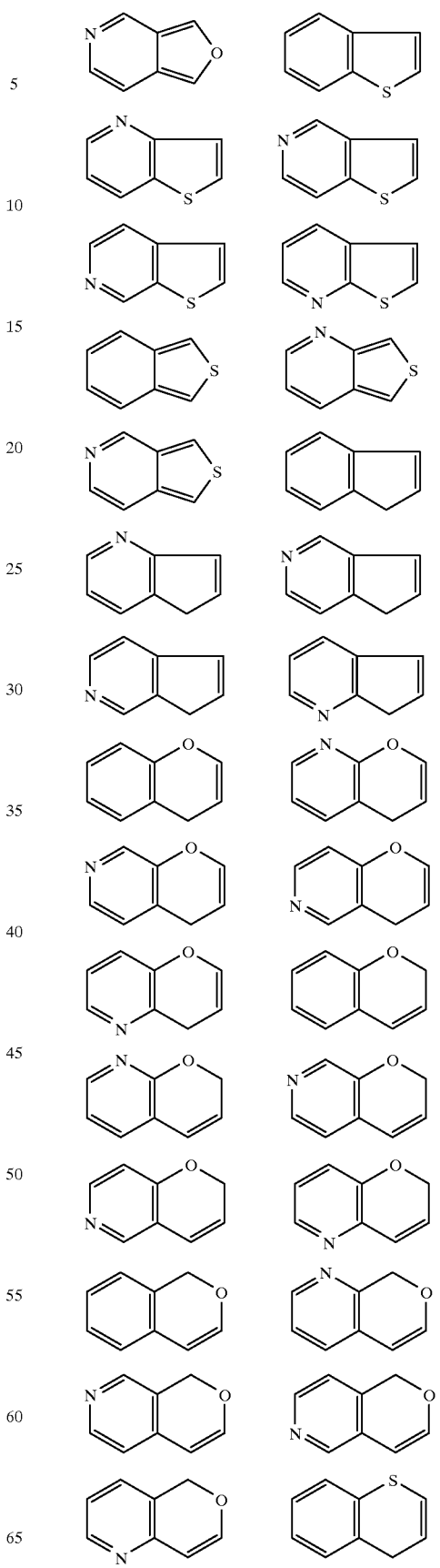

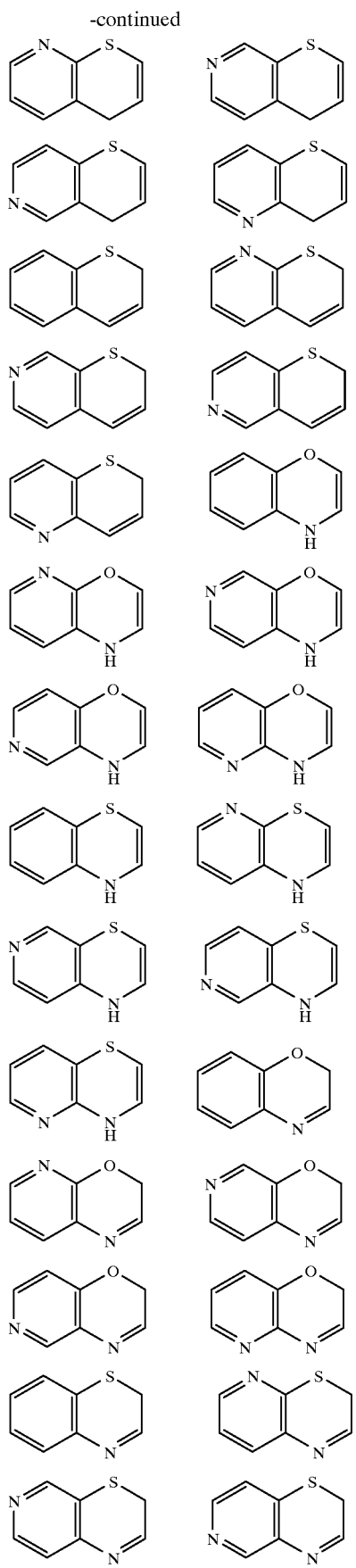
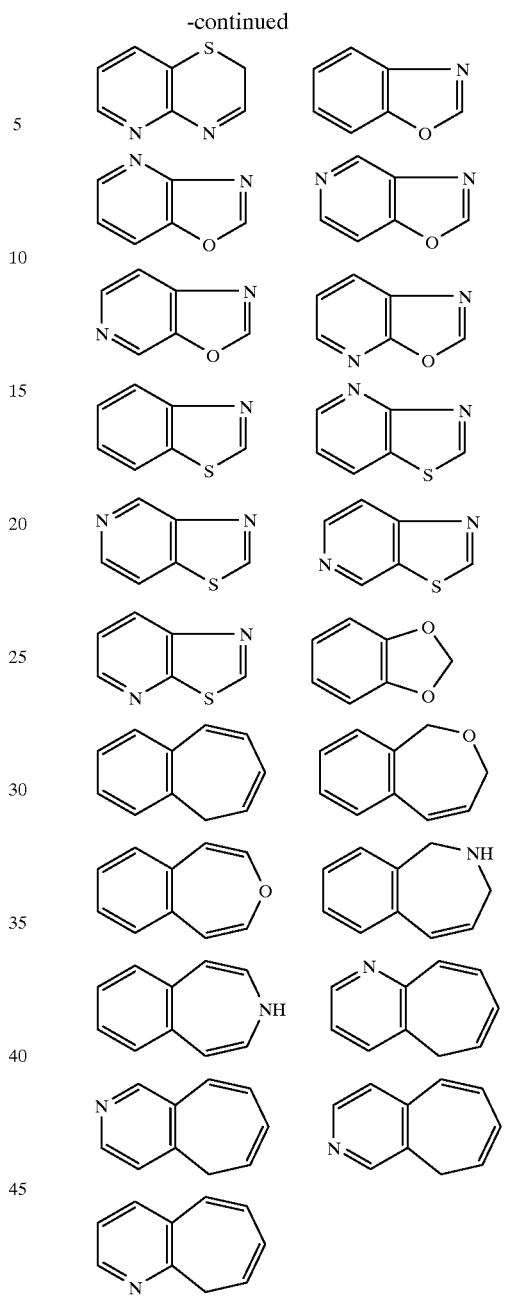

Each of the above rings may have 1 to 3 substituents. When it has two or more substituents, these substituents may be the same or different. Examples of the substituents include hydroxy, oxo, cyano, halogeno, nitro optionally hydroxylated or lower-alkylaminated lower alkyl, lower alkoxy, lower acyl, optionally lower-alkylated carbamoyl and optionally lower-alkylated, lower-acylated, arylsulfonylated or lower-alkylsulfonylated amino.

The term "monocyclic or dicyclic fused aromatic ring" as used in the definition of the ring C means a monocyclic or dicyclic aromatic hydrocarbon or an aromatic heteroring containing one or two nitrogen atoms. It may have one to three substituents on the ring(s).

Examples of the ring C include benzene, pyridine, pyrimidine, naphthalene, quinoline, isoquinoline, indole and quinazoline. These rings may be fused to the ring B at an arbitrary position allowable chemically.

The above-mentioned rings may each have 1 to 3 substituents. When it has two or more substituents, these substituents may be the same or different. Examples of the substituents include halogeno, hydroxy, lower alkyl, lower alkoxy, nitro and optionally lower-alkylated or lower-acylated amino.

The term "lower alkyl group" as used in the definition of the substituents of the rings A and C and in the definition of Y in the above general formula (I) means a linear or branched $C_{1-6}$ alkyl group. Examples thereof include methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, methyl, ethyl, n-propyl and isopropyl groups may be cited as preferable ones and methyl and ethyl groups are the most desirable ones among all.

The term "lower alkylene" as used in the definition of e in Y means a residue obtained by eliminating one hydrogen atom from the lower alkyl group as defined above. When an amino group is substituted by two lower alkyl groups in the definition of the substituents optionally carried by the rings A and C and f in Y, these alkyl groups may be bonded together to form a 5- or 6-membered ring.

The lower alkoxy group in the definition of the substituents optionally carried by the rings A and C means those derived from the above-mentioned lower alkyl groups such as methoxy, ethoxy, n-propoxy, isopropoxy, n-butoxy, isobutoxy and tert-butoxy groups. Among these lower alkoxy groups, methoxy and ethoxy groups may be cited as the most desirable ones. The halogen atom is exemplified by fluorine, chlorine and bromine atoms.

Examples of the lower acyl group include those having 1 to 6 carbon atoms such as formyl, acetyl, propionyl, butyryl, isobutyryl and valeryl groups.

The term "arylsulfonylated or lower-alkylsulfonylated amino" as used in the definition of the substituent optionally carried by the ring A means, for example, an amino group optionally p-toluenesulfonylated, methylsulfonylated or ethylsulfonylated.

Fused polycyclic heterocycle derivatives represented by the above general formula (I) sometimes form salts with acids. The salts of the compounds (I) are also included in the scope of the present invention. Examples of the acid salts include inorganic acid salts such as hydrochloride, hydrobromide, sulfate, etc. and organic acid salts such as acetate, lactate, succinate, fumarate, maleate, citrate, benzoate, methanesulfonate, p-toluenesulfonate, etc.

Needless to say, the present invention also involves hydrates of these compounds and optical isomers thereof, if any. Although the compounds of the present invention show potent antitumor activity, compounds which show antitumor activity when metabolized, for example, oxidized, reduced, hydrolyzed or conjugated in vivo are also involved therein. Moreover, the present invention involves compounds capable of forming the compounds of the present invention when metabolized, for example, oxidized, reduced or hydrolyzed in vivo.

The compounds (I) of the present invention can be produced by various processes. Now typical examples of these production processes will be described.

1) A compound of the general formula (I) can be produced by reacting a compound represented by the following general formula (II):

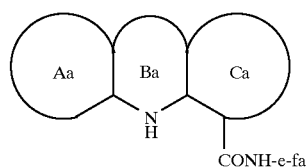

wherein the rings Aa and Ca respectively represent optionally protected rings A and C; the ring Ba represents 4H-1,4-oxazine, 4H-1,4-thiazine, 4(1H)-pyridone or pyrrole; fa means optionally protected f; and e has the same meaning as the one defined above, with a compound represented by the following general formula (III):

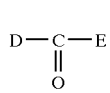

wherein D and E are the same or different and each represents a leaving group.

This reaction is usually effected by dissolving the compound (II) in an aprotic solvent such as dimethylformamide, tetrahydrofuran or dioxane, adding 2 to 3 equivalents of sodium hydride thereto and then adding the compound (III).

Examples of the compound (III) include phosgene, ethyl chlorocarbonate and N,N'-carbonyldiimidazole. This reaction is carried out usually in a temperature range of from −50 to 150° C.

When the product thus obtained is protected at the amino or hydroxyl group, etc., it may be deblocked by a conventional method such as a treatment with an acid or an alkali or catalytic reduction to thereby give the aimed compound (I).

2) A compound (I) can be produced by reacting a compound represented by the general formula (IV):

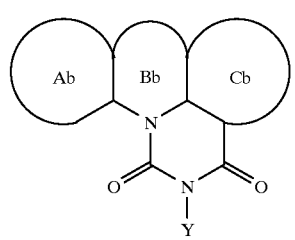

wherein the ring Ab represents a dicyclic fused ring in which at least one of the rings is an aromatic ring and which has a lower acyl or oxo group optionally together with optionally protected substituent(s); the ring Bb represents pyrrole, 4H-1,4-oxazine or 4H-1,4-thiazine; the ring Cb represents a monocyclic aromatic ring optionally having optionally protected substituent(s); and Y is as defined above, with a carbonyl-reducing agent.

The reduction may be effected by using a method commonly employed for reducing carbonyl groups. Preferable examples of such a method include catalytic reduction with the use of a catalyst such as palladium-carbon and reduction with a borane/pyridine complex or sodium borocyanohydride.

Next, a process for producing the starting compounds (II) to be used in the present invention will be described. The starting compounds (II) involve known compounds and novel ones. The novel compounds can be produced by applying or combining processes for synthesizing known compounds which have been already reported.

Production Process 1:

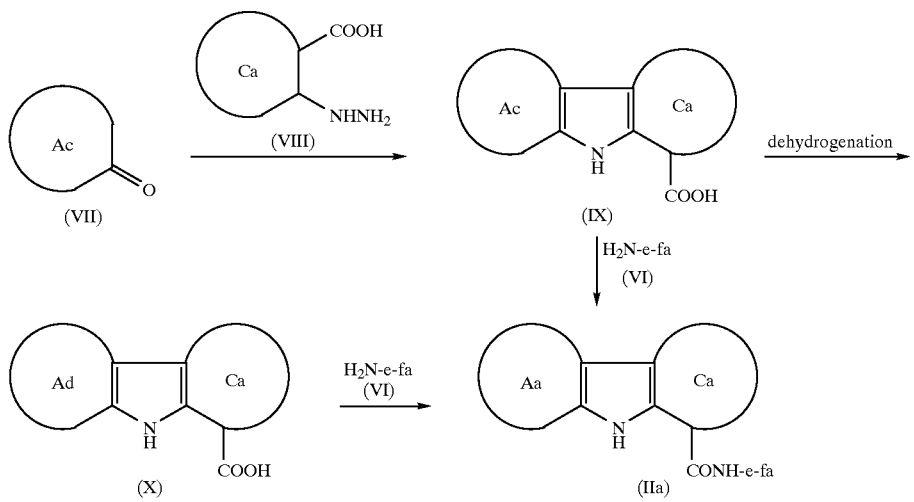

wherein the ring Ac represents an optionally substituted non-aromatic monocyclic ring or a dicyclic fused ring in which both of the rings are non-aromatic ones; the ring Ad represents a ring formed by entirely or partly dehydrogenating the ring Ac; and the ring Ca, e and fa are each as defined above.

The compound represented by the general formula (IX) can be produced by applying, for example, Fischer's method for synthesizing indole or Borsche's method for synthesizing tetrahydrocarbazole [Org. Syn. IV, 884 (1963)]. Namely, it can be obtained by heating a cyclic ketone represented by the formula (VII) and an o-hydrazino aromatic carboxylic acid in acetic acid or formic acid or in a neutral solvent such as ethanol in the presence of an acid catalyst such as hydrochloric acid, sulfuric acid or zinc chloride. When the ring Ac in the compound (IX) is an optionally substituted dicyclic fused ring in which only one of the rings is an aromatic ring, it may be fused with a compound represented by the general formula (VI) to thereby give the aimed compound (IIa). The compound (X) can be produced by partly or entirely dehydrogenating the non-aromatic ring in the compound (IX) with a dehydrogenating agent. As the dehydrogenating agent, use can be made of, for example, 2,3-dichloro-5,6-dicyano-1,4-benzoquinone, chloranil or palladium-carbon. The reaction may be usually effected at room temperature or under heating. When the ring Ac is a dicyclic fused ring in which both of the rings are non-aromatic ones, it is also possible to selectively dehydrogenate one of these rings by appropriately selecting the type and amount of the reagent, reaction conditions, etc. The aimed compound (IIa) can be produced by fusing the compound (X) thus obtained to the compound (VI). The fusing may be carried out by, for example, the acid chloride method, the active ester method or the mixed acid anhydride method or by using fusing agents such as 1,3-dicyclohexylcarbodiimide, N,N'-carbonyldimidazole or diphenylphosporyl azide.

Production Process 2:

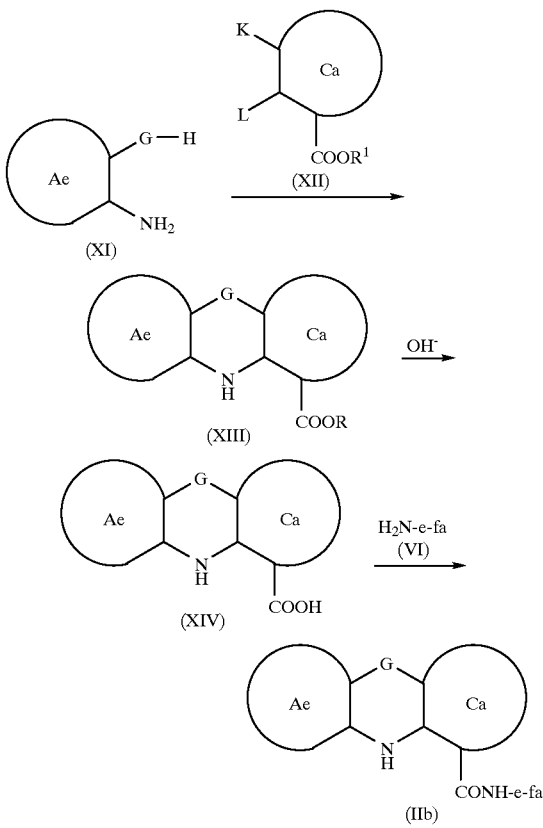

wherein the ring Ae means an optionally substituted monocyclic aromatic ring or a dicyclic fused ring in which at least the ring carrying the substituent —G—H is an aromatic ring; G represents an oxygen atom or a sulfur atom; K and L represent each a leaving group; R represents a lower alkyl group; and the ring Ca, e and fa are each as defined above.

The compound represented by the general formula (XIII) can be produced by reacting the compound of the general formula (XI) with the compound of the general formula (XII). Nitro and halogeno may be cited respectively as preferable examples of the leaving groups K and L in the compound (XII). The reaction may be effected by heating these compounds optionally in the presence of a base such as triethylamine, sodium acetate or sodium hydroxide. The aimed compound (IIb) can be produced by hydrolyzing an ester of the compound (XIII) with an alkali into the compound (XIV) and then fusing this compound to the compound (VI) in the same manner as the one of the production process (I).

When the compound of the present invention is to be used as a medicine, it may be orally or parenterally administered. Although the dose is not particularly restricted but varies depending on the severity of the symptom, the age, sex, body weight and sensitivity of the patient, the method, time and intervals of the administration, the properties, type and active ingredients of the medicinal preparation, etc., it may be usually administered to an adult in a daily dose of from 1 to 3,000 mg, preferably about from 10 to 2,000 mg and still preferably from 20 to 1,000 mg, in one to three portions per day.

To prepare a solid preparation for oral administration, the principal agent is mixed with fillers and, if necessary, binders, disintegrating agents, lubricants, coloring agents, corrigents, etc. and the obtained mixture is processed into tablets, coated tablets, granules, fine subtillaes, dusts, capsules, etc. in a conventional manner.

As the fillers, use can be made of, for example, lactose, cornstarch, sucrose, glucose, sorbitol, crystalline cellulose and silicon dioxide. As the binders, use can be made of, for example, polyvinyl alcohol, ethylcellulose, methylcellulose, acacia, hydroxypropylcellulose and hydroxypropylmethylcellulose. As the lubricants, use can be made of, for example, magnesium stearate, talc and silica. As the coloring agents, use can be made of pharmaceutically acceptable ones. As the corrigents, use can be made of, for example, cocoa powder, menthol, aromatic acids, peppermint oil, Borneo camphor and powdered cinnamon bark. Needless to say, these tablets or granules may be coated with sugar, gelatin, etc., if needed.

To prepare injections, the principal agent is mixed with, if needed, pH regulating agents, buffers, suspending agents, solubilizing agents, stabilizers, isotonizing agents, preservatives, etc. and the obtained mixture is processed into intravenous, subcutaneous or intramuscular injections in a conventional manner. Then these preparations may be freeze-dried in a conventional manner, if necessary.

As the suspending agents, use can be made of, for example, methylcellulose, Polysorbate 80, hydroxyethylcellulose, acacia, powdered tragacanth, sodium carboxymethylcellulose and polyoxyethylene sorbitan monolaurate.

As the solubilizing agents, use can be made of, for example, polyoxyethylene hardened castor oil, Polysorbate 80, nicotinamide, polyoxyethylene sorbitan monolaurate, macrogol and castor oil fatty acid ethyl esters.

As the stabilizers, use can be made of, for example, sodium sulfite and sodium metasulfite. As the preservatives, use can be made of, for example, methyl parahydroxybenzoate, ethyl parahydroxybenzoate, sorbic acid, phenol, cresol and chlorocresol.

Next, pharmacological experimental examples will be given to illustrate the effects of the compounds of the present invention.

EXPERIMENTAL EXAMPLE 1 in vitro Antitumor Test on P388 Cells (Mouse Leukemic Cells)

P388 cells suspended in RPMI1640 medium (manufactured by Sanko Junyaku) containing 10% of fetal calf serum, (100 U/ml) of penicillin, 100 $\mu$g/ml of streptomycin, $5 \times 10^{-5}$M of mercaptoethanol and 1 mM of sodium pyruvate were pipetted into a 96-well U-bottomed microplate at a ratio of $1.25 \times 10^3$ cells (0.1 ml) per well and incubated in a incubator containing 5% of carbon dioxide at 37° C. for a day.

A compound of the present invention was dissolved in dimethyl sulfoxide to give a concentration of $10^{-2}$ M and then diluted with the 10% fetal calf serum-containing RPMI1640 culture medium to give a concentration of $10^{-4}$ or $10^{-5}$ M. By taking this concentration as the maximal level, threefold serial dilution was effected with the use of the 10% fetal calf serum-containing RPMI1640 culture medium. Then these dilutions were added to the P388 incubation plate as described above at a ratio of 0.1 ml per well followed by incubation in an incubator containing 5% of carbon dioxide at 37° C. for 3 days.

After the completion of the incubation, 0.05 ml/well of a 3.3 mg/ml solution of MTT [3-(4,5-dimethylthiazol-2-yl)-2,5-diphenyltetrazolium bromide] was added thereto and the incubation was continued for additional 2 hours. The microplate was centrifuged and the supernatant was aspirated off from each well. Then the formazan thus formed was dissolved in 0.1 ml of dimethyl sulfoxide and the absorbance thereof at 540 nm measured with a microplate reader was taken as an indication of the viable cell count. In accordance with the following formula, the inhibitory ratio was calculated and the 50% inhibitory concentration ($IC_{50}$) of the test compound was determined:

$$\text{inhibitory ratio (\%)} = \frac{C - T}{C} \times 100$$

wherein T means the absorbance of a well containing the test compound; and C means the absorbance of a well containing no test compound.

Table 1 summarizes the $IC_{50}$ data thus obtained.

TABLE 1

| in vitro Antitumor test on P388 cells | | | |
|---|---|---|---|
| Compound(Ex.) | $IC_{50}(\mu M)$ | Compound(Ex.) | $IC_{50}(\mu M)$ |
| 1 | 0.29 | 31 | 0.11 |
| 2 | 0.070 | 32 | 0.41 |
| 3 | 0.026 | 33 | 0.056 |
| 4 | 0.030 | 34 | 0.45 |
| 5 | 0.0048 | 35 | 0.063 |
| 6 | 0.0017 | 36 | 0.014 |
| 7 | 0.031 | 37 | 0.38 |
| 8 | 0.34 | 38 | 0.11 |
| 9 | 0.0067 | 39 | 0.0077 |
| 10 | 0.0085 | 40 | 0.22 |
| 11 | 0.042 | 41 | 0.32 |
| 12 | 0.062 | 42 | 0.049 |
| 14 | 0.074 | 43 | 0.066 |
| 15 | 0.14 | 44 | 0.36 |

TABLE 1-continued in vitro Antitumor test on P388 cells

| Compound(Ex.) | IC$_{50}$($\mu$M) | Compound(Ex.) | IC$_{50}$($\mu$M) |
|---|---|---|---|
| 16 | 0.11 | 45 | 0.16 |
| 17 | 0.034 | 46 | 0.077 |
| 18 | 0.076 | 47 | 0.25 |
| 19 | 0.22 | 48 | 0.35 |
| 20 | 0.57 | 49 | 0.030 |
| 22 | 0.29 | 50 | 0.0071 |
| 23 | 0.081 | 51 | 0.29 |
| 24 | 0.32 | 52 | 0.15 |
| 25 | 0.028 | 53 | 0.30 |
| 26 | 0.23 | 54 | 0.080 |
| 27 | 0.49 | 55 | 0.011 |
| 28 | 0.070 | 56 | 0.015 |
| 29 | 0.071 | 57 | 0.031 |
| 30 | 0.032 | 58 | 0.155 |

EXPERIMENTAL EXAMPLE 2 in vivo Antitumor Test on M5076 (Mouse Reticulum Cell Sarcoma)

M5076 cells (1×10$^6$/animal) were subcutaneously transplanted into the side part of each BDF1 mouse (aged 6 to 7 weeks, female). A compound of the present invention was dissolved in a 5% solution of glucose. From the next day of the transplantation, the solution of the compound was intraperitoneally administered to the animals once a day in accordance with each schedule. On the other hand, a 5% solution of glucose was administered to the control group. The control group had 10 animals, while each test group had 5 animals.

On the 21st day after the transplantation, tumors were taken out and weighed. The tumor multiplication inhibitory ratio of each test group to the control group was determined in accordance with the following formula:

$$\text{inhibitory ratio (\%)} = \frac{C-T}{C} \times 100$$

wherein T means the average tumor weight of the test group; and C means the average tumor weight of the control group.

Table 2 shows the results of this experiment.

TABLE 2 in vivo Antitumor test on M5076

| Compd. (Ex. No.) | Dose (mg/kg/day) | Administration Day (days after transplantation) | Proliferation inhibitory ratio (%) | Survival rate on the judgement day (21th day) |
|---|---|---|---|---|
| 1 | 50 | d1,2,3,4 | 95.2 | 100 |
| 2 | 25 | d9 | 91.4 | 100 |
| 3 | 25 | d9 | 90.0 | 100 |
| 4 | 25 | d9 | 89.2 | 100 |
|  | 12.5 | d1,8,15 | 100 | 100 |
| 8 | 30 | d1,8,15 | 99.9 | 100 |
| 12 | 50 | d1,2,3,4 | 93.9 | 100 |
| 20 | 12.5 | d1,2,3,4 | 70.8 | 100 |
| 26 | 50 | d1,2,3,4 | 97.4 | 100 |
| 33 | 50 | d9 | 74.9 | 100 |
| 35 | 25 | d9 | 78.7 | 100 |
| 52 | 50 | d1,2,3,4 | 70.6 | 100 |

EXPERIMENTAL EXAMPLE 3 in vivo Antitumor Test on MX-1 (Human Mammary Cancer)

MX-1 tumor pieces (about 1 mm$^3$) were subcutaneously transplanted into the side part of each nude mouse (BALB/C.nu/nu, 6 to 7 weeks, female). A compound of the present invention was dissolved in a 5% solution of glucose. When the tumor volume reached 50 mm$^3$ (on the about 10th day after the transplantation), the solution of the compound was intraperitoneally administered to the animals once a day in accordance with each schedule. On the other hand, a 5% solution of glucose was administered to the control group. The control group had 10 animals, while each test group had 5 animals.

On the 22nd day after the transplantation, tumors were taken out and weighed. The tumor multiplication inhibitory ratio of each test group to the control group was determined in accordance with the following formula:

$$\text{inhibitory ratio (\%)} = \frac{C-T}{C} \times 100$$

wherein T means the average tumor weight of the test group; and C means the average tumor weight of the control group.

Table 3 shows the results of this experiment.

TABLE 3 in vivo Antitumor test on MX-1

| Compd. (Ex. No.) | Dose (mg/kg/day) | Administration schedule | Proliferation inhibitory ratio (%) | Survival rate on the judgement day (22th day) |
|---|---|---|---|---|
| 1 | 25 | q4d × 4 | 48.0 | 100 |
| 2 | 25 | q7d × 3 | 63.3 | 100 |
| 3 | 20 | q7d × 3 | 55.7 | 100 |
| 4 | 15 | q7d × 3 | 98.4 | 100 |
| 7 | 15 | q7d × 3 | 73.2 | 100 |
| 8 | 25 | q7d × 3 | 94.0 | 100 |
| 10 | 10 | q7d × 3 | 59.7 | 100 |
| 11 | 30 | q7d × 3 | 82.5 | 100 |

As these experimental data clearly show, the compounds of the present invention have excellent antitumor effects and thus are useful as an antitumor agent.

EXAMPLE

Now, Production Examples showing the production of the starting compounds employed in the present invention and Examples relating to typical examples of the compounds of the present invention will be given. However, it is to be understood that the present invention is not restricted thereto.

Production Example 1

5,6-Dihydro-7H-benzo[c]carboazole-8-carboxylic acid

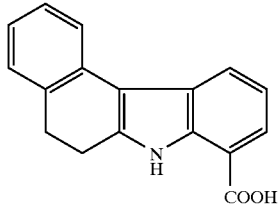

A solution of 5.00 g (34.2 mmol) of β-tetralone in acetic acid (10 ml) was dropped into a suspension of 7.05 g (37.4 mmol) of 2-hydrazinobenzoic acid hydrochloride in acetic acid (40 ml) at 80° C. and the obtained mixture was heated under reflux for 3 hours and 45 minutes. After bringing back to room temperature, water was added thereto and the precipitate thus formed was taken up by filtration, washed with water, dried and recrystallized from ethanol to thereby give 5.2 g of the title compound.

$^1$H-NMR(DMSO-d$_6$) δ (ppm);2.91–3.06(m,4H),7.03(t, J=7.6 Hz,1H),7.17(t,J=7.6 Hz,1H),7.20–7.27(m,2H),7.72 (d,J=7.6 Hz,1H),7.76(d,J=7.6 Hz,1H),8.19(d,J=7.6 Hz, 1H), 11.29(s,1H)

Production Example 2

7H-Benzo[c]carboazole-8-carboxylic acid

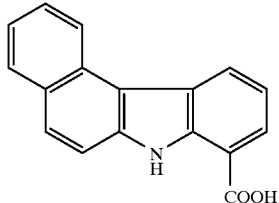

3.29 g (14.3 mmol) of 2,3-dichloro-5,6-dicyano-1,4-benzoquinone was added to a suspension of 2.97 g (11.3 mmol) of the compound of Production Example 1 in benzene (200 ml) at room temperature and the obtained mixture was stirred for 50 minutes and then heated under reflux for 3 hours and 20 minutes. After bringing back to room temperature, the precipitate thus formed was taken up by filtration and recrystallized from ethanol to thereby give 2.76 g of the title compound.

$^1$H-NMR(DMSO-d$_6$) δ (ppm); 7.39(t,J=7.3 Hz,1H),7.48 (t, J=7.3 Hz,1H),7.70(t,J=7.3 Hz,1H),7.93(d,J=8.7 Hz,1H), 8.00–8.07(m,3H),8.79(d,J=7.3 Hz,1H), 8.87(d,J=7.3 Hz, 1H),11.82(s,1H),13.22(br-s,1H)

Production Example 3

N-[2-(Dimethylamino)ethyl]-7H-benzo[c]carboazole-8-carboxamide

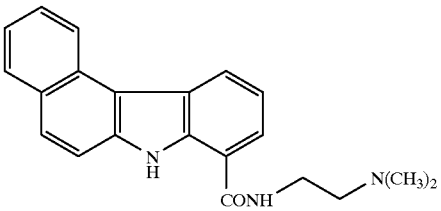

2.52 g (15.5 mmol) of N,N'-carbonyldiimidazole was added to a solution of 1.89 g (7.25 mmol) of the compound of Production Example 2 in dimethylformamide (60 ml) at room temperature and the obtained mixture was stirred for 45 minutes. Then 5.0 ml (45.5 mmol) of N,N-dimethylethylenediamine was added thereto and the resulting mixture was stirred for 2 hours and 40 minutes. After concentrating, it was extracted by adding water and ethyl acetate. The organic layer was taken up, washed with water, dried over sodium sulfate and concentrated to dryness to thereby give 2.47 g of the title compound.

$^1$H-NMR(DMSO-d$_6$) δ (ppm); 2.33(s,6H),2.60(t,J=5.7 Hz, 2H),3.63(q,J=5.7 Hz,2H),7.16(br-s,1H),7.38(t, J=7.5 Hz,1H),7.46–7.50(m,1H),7.65–7.73(m,3H),7.89(d, J=9.0 Hz,1H),8.01(d,J=8.2 Hz,1H),8.69(d,J=7.5 Hz,1H), 8.74(d, J=8.2 Hz,1H),10.94(br-s,1H)

Production Example 4

3-Acetyl-7H-benzo[c]carbazole-8-carboxylic acid

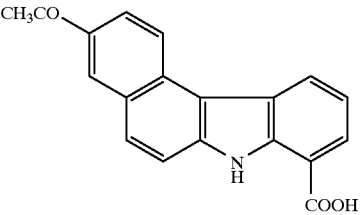

1.17 ml (12.4 mmol) of acetic anhydride was added to a suspension of 5.1 g (38 mmol) of aluminum chloride in dichloromethane (300 ml) at 0° C. and the obtained mixture was stirred for 20 minutes. Next, 2.16 g (8.28 mmol) of the compound of Production Example 2 was added thereto and the obtained mixture was stirred at the same temperature for 4 hours and 30 minutes. Then the reaction mixture was poured into ice-water and extracted with a mixture of chloroform with ethanol. The organic layer was taken up and concentrated. The residue was purified by silica gel column chromatography to thereby give 1.45 g of the title compound.

$^1$H-NMR(DMSO-d$_6$) δ (ppm); 2.72(s,3H),7.44(t,J=7.6 Hz, 1H),8.07(d,J=7.6 Hz,1H),8.11(d,J=9.1 Hz,1H),8.14(d, J=9.1 Hz,1H),8.18(dd,J=1.9,8.8 Hz,1H),8.79(d,J=1.9 Hz,1H),8.87(d,J=8.8 Hz,1H),8.91(d,J=7.6 Hz,1H),12.01(s, 1H)

Production Example 5

3-Acetyl-N-[2-(dimethylamino)ethyl]-7H-benzo[c]carbazole-8-carboxamide

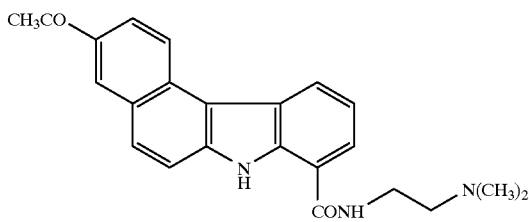

291 mg (1.80 mmol) of N,N'-carbonyldiimidazole was added to a solution of 247 mg (0.815 mmol) of the compound of Production Example 4 in dimethylformamide (7 ml) under ice-cooling. After bringing back to room temperature, the obtained mixture was stirred for about 2 hours. Next, 0.45 ml (4.1 mmol) of N,N-dimethylethylenediamine was added thereto and the reaction mixture was brought back to room temperature and stirred at room temperature for about 12 hours. After extracting by adding water and chloroform, the organic layer was taken up, dried over sodium sulfate and concentrated to dryness. Then the residue was purified by silica gel column chromatography to thereby give 140 mg of the title compound.

$^1$H-NMR(DMSO-$d_6$) δ (ppm); 2.29(s,6H),2.53–2.61(m,2H), 2.74(s,3H),3.52(q,J=5.9 Hz,2H),7.43(t,J=7.1 Hz,1H), 7.97(d,J=7.1 Hz,1H),8.10(d,J=8.7 Hz,1H), 8.14(d, J=8.7 Hz,1H),8.20(dd,J=1.8,8.5 Hz,1H),8.72(t,J=5.9 Hz,1H), 8.79–8.83 (m,2H),8.88(d,J=8.5 Hz,1H),12.17(s,1H)

Production Example 6

3,4,5,8-Tetrahydronaphthalene-1,6(2H,7H)-dione

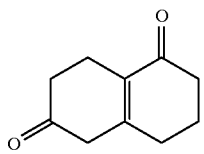

6.8 g (38.2 mmol) of 1,2,3,4,5,8-hexahydro-1-oxo-6-methoxynaphthalene was dissolved in 50 ml of tetrahydrofuran and 5 ml of 1 N hydrochloric acid was added thereto. After stirring at room temperature for 1 hour, ethyl acetate was added thereto. Then the reaction mixture was washed with a saturated aqueous solution of sodium chloride and dried over magnesium sulfate. After concentrating, a small amount of a mixture of n-hexane with ethyl acetate (1:1) was added thereto and the obtained mixture was cooled in a dry ice-ether bath. The precipitate thus formed was recovered by filtration and washed with a small amount of n-hexane to thereby give 4.8 g of the title compound.

$^1$H-NMR(CDCl$_3$) δ (ppm); 2.01–2.11(m,2H),2.30–2.37 (m,2H),2.45–2.51(m,4H),2.68–2.76(m,2H),3.05(s,2H)

Production Example 7

4-Oxo-1,2,3,4-tetrahydro-7H-benzo[c]carbazole-8-carboxylic acid

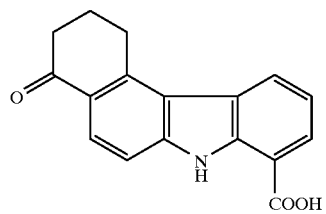

5.4 g (28.6 mmol) of 2-hydrazinobenzoic acid hydrochloride and 4.7 g (34.3 mmol) of zinc chloride were added to 300 ml of glacial acetic acid. Under stirring at about 85° C., 4.7 g (28.6 mmol) of the compound of Production Example 6 was added thereto over about 5 minutes. Then the obtained mixture was stirred at the same temperature for about 2 hours, brought back to room temperature and the precipitate was recovered by filtration. After concentrating the filtrate, water was added thereto and the precipitate thus formed was recovered by filtration. These precipitates were combined, dried and then dissolved in about 500 ml of dimethylformamide. Under stirring at room temperature, a solution of 6.5 g (28.6 mmol) of 2,3-dichloro-5,6-dicyano-1,4-benzoquinone in tetrahydrofuran (20 ml) was added thereto and the obtained mixture was stirred for about 30 minutes. After concentrating, about 50 ml of ethanol was added and the precipitate thus formed was recovered by filtration to thereby give 3.4 g of the title compound.

$^1$H-NMR(DMSO-$d_6$) δ (ppm); 2.17–2.29(m,2H), 2.63–2.70 (m,2H),3.55(t,J=6.0 Hz,2H),7.36(t,J=7.6 Hz,1H), 7.73(d, J=8.8 Hz,1H),8.03(d,J=8.8 Hz,1H),8.06(dd,J=0.8, 7.6 Hz, 1H),8.48(dd,J=0.8,7.6 Hz,1H),11.83(s,1H),13.33 (br-s,1H)

Production Example 8

N-[2-(Dimethylamino)ethyl]-4-oxo-1,2,3,4-tetrahydro-7H-benzo[c]carbazole-8-carboxamide

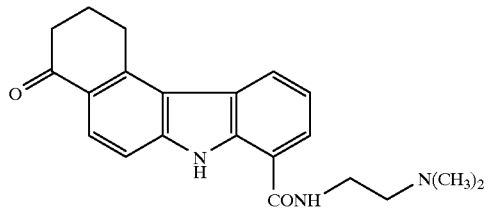

3.4 g (12.2 mmol) of the compound of Production Example 7 was added to 120 ml of dimethylformamide and stirred. Next, a solution of 3.0 g (18.5 mmol) of N,N'-carbonyldiimidazole in dimethylformamide (30 ml) was added thereto. After stirring at room temperature for 1 hour, 3.2 g (36.3 mmol) of N,N-dimethylethylenediamine was added thereto. After stirring at the same temperature for additional 1 hour, the reaction mixture was concentrated and ethyl acetate was added thereto. Then it was washed successively with dilute aqueous ammonia and an aqueous solution of sodium chloride, dried over magnesium sulfate and concentrated to dryness to thereby give 4.3 g of the title compound.

FAB mass spectrometry m/z: 350 ([M+H]⁺). ¹H-NMR (CDCl₃) δ (ppm); 2.30–2.40(m⁺s,2H+6H),2.62(t, J=6.0 Hz,2H),2.74–2.79(m,2H),3.56–3.66(m,4H),7.21 (br-s,1H), 7.32(t,J=8.0 Hz;1H),7.41(d,J=8.4 Hz,1H), 7.70(dd,J=0.8,8.0 Hz,1H),8.25(d,J=8.4 Hz,1H),8.33(dd,J=0.8,8.0 Hz,1H), 10.91(br-s,1H)

Production Example 9

2,3-Dihydro-3-oxo-1H,6H-cyclopenta[c]carbazole-7-carboxylic acid

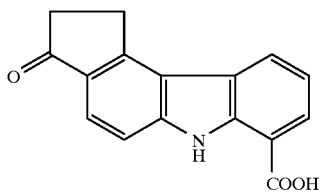

The title compound was obtained by reacting 2,3,4,7-tetrahydro-1H-indene-1,5(6H)-dione, which had been synthesized from 2,3,4,7-tetrahydro-5-methoxy-1H-inden-1-one by the same method as the one of Production Example 6, in the same manner as the one of Production Example 7.

FAB mass spectrometry m/z: 266 ([M+H]⁺). ¹H-NMR (DMSO-d₆) δ PPM); 2.70–2.82(m, 2H) 3.52–3.62 (m,2H), 7.41(t,J=7.6 Hz,1H),7.70(d,J=8.4 Hz,1H),7.81(d, J=8.4 Hz,1H),8.09(dd,J=0.8,7.6 Hz,1H), 8.39(d,J=7.6 Hz, 1H), 11.95(s,1H),13.37(br-s,1H)

Production Example 10

2,3-Dihydro-N-[2-(dimethylamino)ethyl]-3-oxo-1H,6H-cyclopenta-[c]carbazole-7-carboxamide

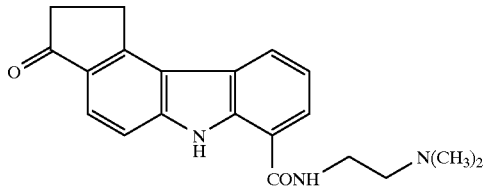

The title compound was obtained from the compound of Production Example 9 by the same method as the one of Production Example 8.

FAB mass spectrometry m/z: 336 ([M+H]⁺). ¹H-NMR (CDCl₃) δ (ppm); 2.34(s,6H),2.61(t,J=6.0 Hz,2H), 2.85–2.91(m,2H),3.58–3.66(m,4H),7.18(br-s,1H),7.36 (t,J= 7.6 Hz,1H),7.49(d,J=8.4 Hz,1H),7.71(d,J=7.6 Hz, 1H),7.88 (d,J=8.4 Hz,1H),8.22(d,J=7.6 Hz,1H),10.95 (br-s,1H)

Production Example 11

Methyl 5,6,7,8-tetrahydro-9H-carbazole-1-carboxylate

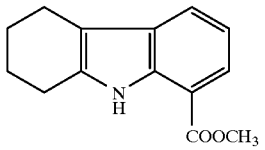

A solution of 28 ml (0.270 mol) of cyclohexanone in acetic acid (100 ml) was dropped into a suspension of 52 g (0.276 mol) of 2-hydrazinobenzoic acid hydrochloride in acetic acid (500 ml) at 100° C. and the obtained mixture was heated under reflux for 6 hours. After bringing back to room temperature, 1 l of water was added thereto and the precipitate thus formed was taken up by filtration, washed with water and dried to thereby give 43 g of a powder. This powder was then dissolved in 500 ml of acetone. After adding 37.5 ml (0.602 mol) of methyl iodide and 41.4 g (0.300 mol) of anhydrous potassium carbonate thereto, the reaction mixture was heated under reflux for 2 hours. After bringing back to room temperature, the insoluble matters were filtered off. After concentrating the filtrate, water was added thereto and the precipitate thus formed was recovered by filtration to thereby give 45.7 g of the title compound.

¹H-NMR(CDCl₃) δ (ppm); 1.85–1.97(m,4H),2.70–2.74 (m,2H), 2.76–2.80(m,2H),3.97(s,3H),7.09 (t,J=7.6 Hz,1H), 7.65–7.68(m,1H),7.79(dd,J=1.1,7.6 Hz, 1H),9.39(br-s,1H)

Production Example 12

Methyl 5-oxo-5,6,7,8-tetrahydro-9H-carbazole-1-carboxylate

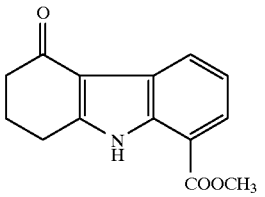

45.7 g (0.199 mol) of the compound of Production Example 11 was dissolved in a mixture of tetrahydrofuran (500 ml) with water (50 ml). Into the obtained solution was dropped a solution of 90.8 g (0.400 mol) of 2,3-dichloro-5,6-dicyano-1,4-benzoquinone in tetrahydrofuran (200 ml) in a nitrogen atmosphere under ice-cooling. After stirring at room temperature for 3 hours, 1 l of an aqueous solution of potassium carbonate was added thereto followed by extraction with ethyl acetate. Then the organic layer was taken up, washed with water, dried over magnesium sulfate and concentrated. The residue was recrystallized from ethanol to thereby give 39.7 g of the title compound.

¹H-NMR(DMSO-d₆) δ (ppm); 2.10–2.17(m,2H), 2.44–2.48 (m,2H),3.07(t,J=6.2 Hz,2H),3.96(s,3H),7.28(t,J= 7.7 Hz, 1H),7.81(dd,J=1.3,7.7 Hz,1H),8.25(dd,J=1.3,7.7 Hz,1H), 11.79(br-s,1H)

Production Example 13

Methyl 5-hydroxy-9H-carbazole-1-carboxylate

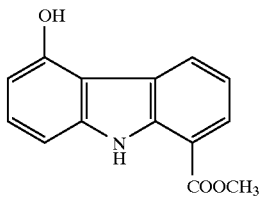

39.1 g (0.161 mol) of the compound of Production Example 12 was suspended in diphenyl ether (150 ml). After adding 10 g of 10% palladium-carbon, the obtained mixture was heated under reflux in a nitrogen atmosphere for 3 hours. After allowing to cool, the crystals thus precipitated and the palladium-carbon were recovered by filtration and washed with hexane. Then the recovered mixture was dissolved in hot tetrahydrofuran and the palladium-carbon was filtered off. After concentrating, the residue was recrystallized from ethanol to thereby give 34.7 g of the title compound.

$^1$H-NMR(CDCl$_3$) δ (ppm); 4.03(s,3H),5.54(s,1H),6.62 (dd,J=0.6,7.9 Hz,1H),7.10(dd,J=0.6,7.9 Hz,1H),7.27(t,J=7.9 Hz,1H),7.30(t,J=7.9 Hz,1H),8.05(dd,J=1.2,7.9 Hz, 1H), 8.46–8.50(m,1H),9.93(br-s,1H)

Production Example 14

[1-Methoxycarbonyl-9H-carbazol-5-yl]oxyacetic acid

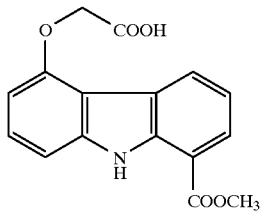

34.8 g (0.144 mol) of the compound of Production Example 13 was dissolved in acetone (550 ml). After adding 68.5 ml (0.432 mol) of benzyl bromoacetate, 64.8 g (0.432 mol) of sodium iodide and 29.8 g (0.216 mol) of anhydrous potassium carbonate thereto, the obtained mixture was heated under reflux for 60 hours. After allowing to cool, the precipitate thus formed was filtered off followed by concentration. Then it was extracted by adding ethyl acetate and water and the organic layer was taken up, washed with water, dried over magnesium sulfate and concentrated. To the obtained residue was added n-hexane so as to solidify the same. Then it was recovered by filtration and recrystallized from ethanol to thereby give 40.7 g of benzyl ester of the title compound. This product was suspended in a mixture of tetrahydrofuran (600 ml) and methanol (500 ml). Next, 12 g of 10% palladium-carbon was added thereto and the product was hydrogenated under atmospheric pressure at an ordinary temperature to thereby give 29.4 g of the title compound.

$^1$H-NMR(CD$_3$OD) δ (ppm); 4.02 (s, 3H) 4.90 (s, 2H),6.67 (dd,J=0.6,8.0 Hz,1H),7.23(t,J=7.7 Hz,1H),7.26(dd, J=0.6, 8.0 Hz,1H),7.35(t,J=8.0 Hz,1H),8.02(dd,J=1.1, 7.7 Hz,1H), 8.63(dd,J=1.1,7.7 Hz,1H),10.87(br-s,1H)

Production Example 15

2,3-Dihydro-3-oxo-6H-furo[3,2-c]carbazole-7-carboxylic acid

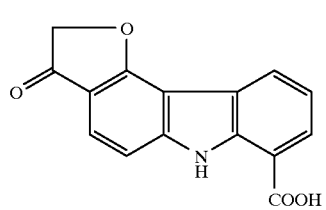

29.4 g (0.098 mol) of the compound of Production Example 14 was suspended in toluene (500 ml). After adding 36 ml (0.494 mol) of thionyl chloride, the obtained mixture was heated under reflux until it became homogeneous. After concentrating, it was dissolved by adding 500 ml of dichloromethane thereto and 32.1 g (0.240 mol) of aluminum chloride was added in portions thereto while stirring under ice-cooling. Then it was brought back to room temperature and stirred overnight and then ice-water was added thereto under ice-cooling. After stirring at room temperature, it was concentrated and dilute hydrochloric acid was added thereto. The precipitate was recovered by filtration, washed successively with water and ethanol and dried to thereby give 26.5 g of a powder. The whole powder was dissolved in a mixture of tetrahydrofuran (350 ml) with methanol (250 ml) and then 750 ml of a degassed 0.2 N aqueous solution of sodium hydroxide was added thereto in a nitrogen atmosphere. After hydrolyzing the ester at 50° C., 20 ml of conc. hydrochloric acid was added thereto. Then it was extracted with a mixture of ethyl acetate with tetrahydrofuran and the organic layer was taken up, washed with water, dried over magnesium sulfate and concentrated. The residue was purified by silica gel column chromatography to thereby give 11.4 g of the title compound.

$^1$H-NMR(DMSO-d$_6$) δ (ppm); 5.00(s,2H),7.41(t,J=7.7 Hz, 1H),7.56(d,J=8.5 Hz, 1H),7.63(d,J=8.5 Hz,1H),8.07 (dd,J=1.3,7.7 Hz,1H),8.29–8.32(m,1H),12.10(br-s,1H)

Production Example 16

N-[2-(Allylmethylamino)ethyl-4-oxo-1,2,3,4-tetrahydro-7H-benzo[c]carbazole-8-carboxymide

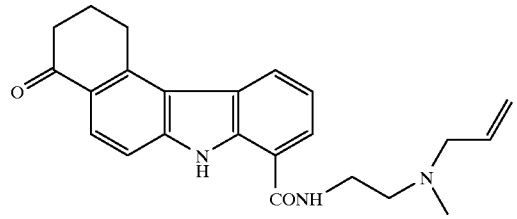

Starting with 0.5 g (1.79 mmol) of the compound of Production Example 7 and 0.53 g (7.15 mmol) of N-methylethylenediamine, 0.49 g of N-[2-(methylamino) ethyl]-4-oxo-1,2,3,4-tetrahydro-7H-benzo[c]carbazole-8-carboxamide was obtained by the same method as the one of Production Example 8. 0.49 g (1.46 mmol) of this product, 0.25 g (1.74 mmol) of allyl bromide and 0.23 g (1.78 mmol) of N,N-diisopropylethylamine were dissolved in tetrahydrofuran (30 ml) and stirred at 55° C. for about 5 hours. After allowing to cool, it was diluted with ethyl acetate, washed successively with dilute aqueous ammonia and an aqueous solution of sodium chloride, dried over magnesium sulfate and concentrated. The residue was purified by preparative thin layer chromatography to thereby give 0.24 g of the title compound.

$^1$H-NMR(CDCl$_3$) δ (ppm); 2.28–2.40(m+s,2H+3H),2.70 (t,J=6.0 Hz,2H),2.73–2.80(m,2H),3.11–3.17(m,2H), 3.56–3.68(m,4H),5.17–5.29(m,2H),5.82–5.97(m,1H), 7.24 (br-s,1H),7.33(t,J=7.6 Hz,1H),7.42(d,J=8.4 Hz, 1H),7.67 (dd,0.8,7.6 Hz,1H),8.25(d,J=8.4 Hz,1H),8.33 (dd,J=0.8,7.6 Hz,1H),10.88(br-s,1H)

Production Example 17

5-[1-(Allylmethylamino)ethyl]-12,13-dihydro-4H-benzo[c]pyrimido[5,6,1-jk]carbazole-4,6,10(5H,11H)-trione

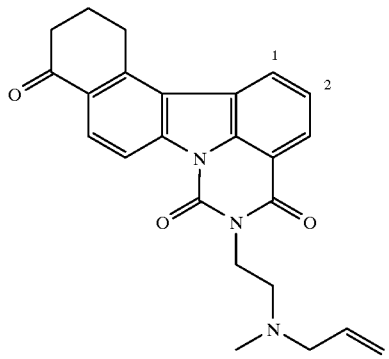

Starting with 0.24 g (0.64 mmol) of the compound of Production Example 16, 0.23 g of the title compound was obtained by the same method as the one of Example 2 while omitting the procedure relating to the hydrochloride.

$^1$H-NMR(CDCl$_3$)δ (ppm); 2.32–2.42(m+s,2H+3H), 2.73–2.84(m,4H),3.10–3.15(m,2H),3.53(t,J=6.4 Hz,2H), 4.35 (t,J=7.2 Hz,2H),5.08–5.22(m,2H),5.74–5.90(m,1H), 7.63 (t,J=7.6 Hz,1H),8.19(dd,J=0.8,7.6 Hz,1H),8.32(dd, J=0.8,7.6 Hz,1H),8.35(d,J=8.4 Hz,1H),8.51(d,J=8.4 Hz, 1H)

Production Example 18

Methyl 6-methyl-9H-carbazole-1-carboxylate

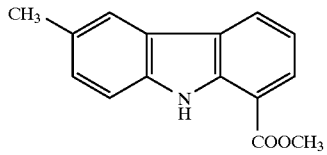

A suspension of 2.0 g (10.6 mmol) of 2-hydrazinobenzoic acid hydrochloride in acetic acid (20 ml) was slowly boiled under stirring and 1.2 ml (9.8 mmol) of 4-methylcyclohexanone was dropped thereinto. The obtained mixture was heated under reflux for 8 hours and then allowed to cool. After adding water, the precipitate thus formed was recovered by filtration, washed with water and dried to thereby give 1.96 g of 6-methyl-5,6,7,8-tetrahydro-9H-carbazole-1-carboxylic acid. This product was dissolved in acetone (50 ml) and 2.1 ml (34 mmol) of methyl iodide and 2.35 g (17 mmol) of anhydrous potassium carbonate were added thereto. The reaction mixture was heated under reflux under stirring for 2 hours, then allowed to cool and extracted with water and ethyl acetate. The organic layer was taken up, washed with water, dried over magnesium sulfate and concentrated to dryness. Thus 1.49 g of methyl 6-methyl-5,6,7,8-tetrahydro-9H-carbazole-1-carboxylate was obtained. This product was suspended in diphenyl ether (10 ml) and 890 mg of 10% palladium-carbon was added thereto. The obtained mixture was heated under reflux under stirring in a nitrogen atmosphere for 1 hour. After allowing to cool, It was dissolved by adding tetrahydrofuran. Then the catalyst was filtered off and the filtrate was concentrated. After adding n-hexane, the crystals thus formed were recovered by filtration to thereby give 1.26 g of the title compound.

$^1$H-NMR(CDCl$_3$) δ (ppm); 2.54(s,3H),4.02(s,3H),7.22 (t,J=7.8 Hz,1H),7.27–7.31(m,1H),7.41(d,J=8.2 Hz,1H), 7.87–7.90(m,1H),8.05(dd,J=1.1,7.8 Hz,1H),8.21–8.25 (m,1H),9.82(br-s,1H)

Production Example 19

Methyl 6-formyl-9H-carbazole-1-carboxylate

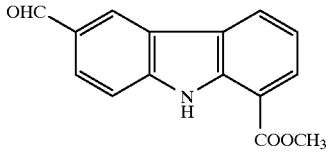

1.8 g (10 mmol) of N-bromosuccinimide and 220 mg (1.3 mmol) of α,α'-azobisisobutyronitrile were added to a solution of 1.2 g (5 mmol) of the compound of Production Example 18 in carbon tetrachloride (100 ml) and the obtained mixture was heated under reflux under stirring for 1 hour. After allowing to cool, the mixture was concentrated and the residue was purified by silica gel column chromatography to thereby give 1.13 g of the title compound.

$^1$H-NMR(CDCl$_3$) δ (ppm); 4.05(s,3H),7.36(t,J=7.8 Hz,1H), 7.62(d,J=8.4 Hz, 1H),8.03(dd,J=1.6,8.4 Hz,1H), 8.14 (dd,J=1.2,7.8 Hz,1H),8.32–8.36(m,1H),8.62–8.64 (m,1H),10.12(s,1H),10.23(br-s,1H)

Production Example 20

Methyl 1,2-dihydro-1-oxo-7H-pyrido[4,3-c]carbazole-8-carboxylate

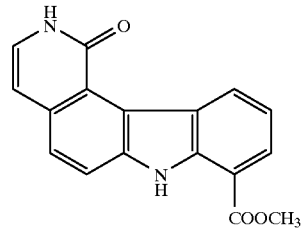

2.6 g (25 mmol) of malonic acid and 0.3 ml of piperidine were added to a solution of 2.0 g (7.9 mmol) of the compound of Production Example 19 in pyridine (80 ml) and the obtained mixture was stirred in a bath at 80° C. for 1 hour. Then 2.6 g (25 mmol) of malonic acid was added thereto under heating and stirring over 1 hour and the obtained mixture was heated under reflux for additional 1 hour. After allowing to cool, the reaction mixture was poured into conc. hydrochloric acid-ice and the precipitate thus formed was recovered by filtration, washed with water and dried to thereby give 1.8 g of 3-(1-methoxycarbonyl-9H-carbazol-6-yl)acrylic acid. The obtained compound was dissolved in acetone (70 ml) and 2 ml of triethylamine was added thereto. Under ice-cooling and stirring, 0.64 ml (6.7 mmol) of ethyl chloroformate was dropped thereinto and then the reaction mixture was stirred at the same temperature for 1 hour. Next, a solution of 870 mg (12 mmol) of sodium azide (90%) in 20 ml of water was dropped thereinto under ice-cooling and stirring. The reaction mixture was stirred at the same temperature for 1 hour and then poured into ice. The precipitate thus formed was recovered by filtration. This precipitate was added together with 3 ml of tributylamine to diphenyl ether (20 ml) and heated to 260° C. After allowing to cool, hexane was added thereto and the precipitate thus formed was recovered by filtration and washed successively with n-hexane and ethanol to thereby give 1.39 g of the title compound.

$^1$H-NMR(DMSO-d$_6$) δ (ppm);4.01(s,3H),6.73(d,J=7.0 Hz, 1H),7.18–7.24(m,1H),7.31(t,J=7.9 Hz,1H),7.77 (d,J= 8.5 Hz,1H),8.08(dd,J=1.3,7.9 Hz,1H),8.22 (d,J=8.5 Hz,1H), 10.13(dd,J=1.3,7.9 Hz,1H),11.36–11.42(m,1H),11.93(br-s, 1H)

Production Example 21

Methyl 7H-pyrido[4,3-c]carbazole-8-carboxylate

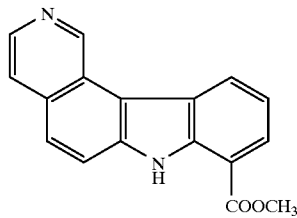

10 ml of phosphorus oxychloride was added to 1.19 g (4 mmol) of the compound of Production Example 20 and the obtained mixture was heated under reflux. 3 hours thereafter, the reaction mixture was poured into ice and neutralized with sodium bicarbonate. Then it was extracted with dichloromethane. The organic layer was taken up, washed with water, dried over magnesium sulfate and concentrated. The residue was purified by silica gel column chromatography to thereby give 390 mg of methyl 1-chloro-7H-pyrido[4,3-c] carbazole-8-carboxylate. This product was dissolved in a mixture of tetrahydrofuran with methanol and 1 ml of triethylamine was added thereto. Then hydrogenation was effected in the presence of palladium-carbon under atmospheric pressure at an ordinary temperature to thereby give 300 mg of the title compound.

$^1$H-NMR(DMSO-d$_6$) δ (ppm);4.04(s,3H),7.48(t,J=7.7 Hz, 1H),8.00(d,J=5.4 Hz,1H),8.02(d,J=8.8 Hz,1H),8.14(d, J=7.7 Hz,1H),8.28(d,J=8.8 Hz,1H),8.58(d,J=5.4 Hz,1H), 9.06(d,J=7.7 Hz,1H),10.22(s,1H),12.11(br-s,1H)

Production Example 22

10-Nitro-7H-benzo[c]phenothiazine-8-carboxylic acid

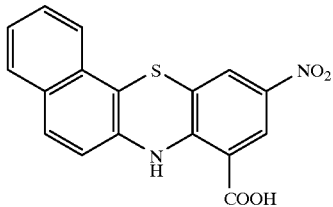

5 ml of a 2 N aqueous solution of sodium hydroxide was added to a solution of 1.7 g (9.73 mmol) of 2-amino-1-naphthalenethione in ethanol (30 ml) and the obtained mixture was heated under reflux. To this mixture was added 2.54 g(9.76 mmol) of methyl 2-chloro-3,5-dinitrobenzoate and the obtained mixture was heated under reflux for 1 hour. To this mixture were added 10 ml of a 2 N aqueous solution of sodium hydroxide and 40 ml of ethanol and the obtained mixture was heated under reflux for additional 10 hours. Then it was brought back to room temperature and concentrated. After adding water, 1 N hydrochloric acid was slowly added thereto under stirring to thereby regulate the pH value to about 1. The precipitate was recovered by filtration and washed successively with ethanol and methanol to thereby give 1.14 g of the title compound.

$^1$H-NMR(DMSO-d$_6$) δ (ppm); 7.04(d,J=8.4 Hz,$_1$H),7.40 (t,J=8.4 Hz,1H),7.55(t,J=8.4 Hz,1H),7.64(d,J=8.4 Hz, 1H), 7.68(d,J=8.4 Hz,1H),7.82(d,J=8.4 Hz,1H),7.90(s, 1H),8.35 (s,1H),11.37(br-s,1H)

Production Example 23

N-[2-(Dimethylamino)ethyl]-10-nitro-7H-benzo[c] phenothiazine-8-carboxamide

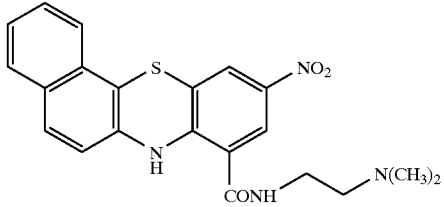

10 ml of phosphorus trichloride and 2 ml of dimethylformamide were successively added to a suspension of 1.82 g (5.39 mmol) of the compound of Production Example 22 in chloroform (60 ml) at 0° C. Then it was slowly brought back to room temperature and stirred overnight. After completely distilling off the solvent from the mixture under reduced pressure, 30 ml of dichloromethane was added to the residue. While stirring at 0° C., a solution of 5 ml of N,N-dimethylethylenediamine in dichloromethane (30 ml) was dropped into the mixture. Then the reaction mixture was slowly brought back to room temperature and stirred at room temperature for 7 hours. Next, water and a saturated aqueous solution of sodium hydrogencarbonate were added thereto and the obtained mixture was stirred and filtered through celite to thereby eliminate the insoluble matters therefrom. The organic layer was taken up, washed successively with water and a saturated aqueous solution of sodium chloride, dried over anhydrous magnesium sulfate, concentrated to dryness and recrystallized from ethanol to thereby give 956 mg of the title compound.

$^1$H-NMR(DMSO-d$_6$) δ (ppm); 2.20(s,6H),2.45(t,J=6.0 Hz,2H),3.37(t,J=6.0 Hz,2H), 7.06(d,J=8.4 Hz,1H),7.41(t,J=8.4 Hz,1H),7.56(t, J=8.4 Hz,1H),7.66(t,J=8.4 Hz,1H),7.69 (d,J=8.4 Hz,1H), 7.83(d,J=8.4 Hz,1H),7.93(br-s,1H),8.39(d, J=2.9 Hz, 1H),9.50(br-s,1H)

Production Example 24

3-(4-Methylbenzenesulfonamido)-7H-benzo[c]carbazole-8-carboxylic acid

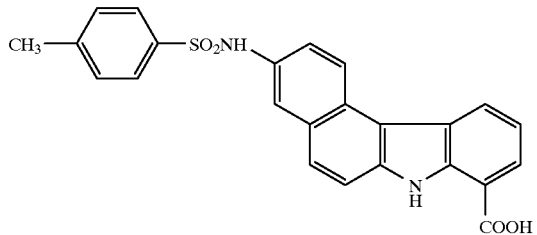

The title compound was obtained by reacting 5,6-dihydro-3-(4-methylbenzenesulfonamido)-7H-benzo[c]carbazole-8-carboxylic acid, which had been obtained by heating under reflux 6-(4-methylbenzenesulfonamido)-2-tetralone and 2-hydrazinobenzoic acid hydrochloride in xylene, in the same manner as the one of Production Example 2.

$^1$H-NMR(DMSO-d$_6$) δ (ppm); 2.26(s,3H),7.29(d, J=8.0 Hz,2H),7.35(dt,J=2.0,7.6 Hz,1H),7.46(d,J=8.8 Hz,1H),7.66 (d,J=6.8 Hz,2H),7.71(s,1H),7.79(d,J=9.2 Hz, 1H),7.96(dd, J=2.0,9.2 Hz,1H),8.01(d,J=8.8 Hz,1H),8.66(d,J=8.8 Hz,1H), 8.79(d,J=8.0 Hz,1H),10.33(s,1H),11.76(s, 1H)

Production Example 25

Ethyl 13H-benz[6,7]indolo[2,3-c]quinoline-12-carboxylate

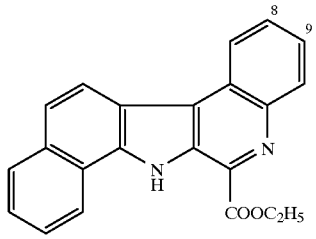

A suspension of 4.24 g (22.5 mmol) of 1-naphthylhydrazine hydrochloride in acetic acid (35 ml) was slowly boiled and a solution of 3.4 g (20.6 mmol) of 2-nitrophenylacetaldehyde in acetic acid (15 ml) was dropped thereinto under stirring. After the completion of the dropping, the obtained mixture was heated under reflux for 1 hour. Then 20 ml of a mixture of 1 N hydrochloric acid with acetic acid was further added thereto and the obtained mixture was heated under reflux for additional 1 hour. After distilling off the solvent, the residue was dissolved by adding ethyl acetate thereto. The organic layer was washed successively with an aqueous solution of sodium hydrogencarbonate, water and a saturated aqueous solution of sodium chloride and dried over anhydrous magnesium sulfate. After distilling off the solvent, the residue was purified by silica gel column chromatography to thereby give 1.91 g (yield: 32%) of 7-(2-nitrophenyl)benz[g]indole. Then the obtained product was dissolved in ethyl acetate (60 ml) and 200 mg of platinum (IV) oxide was added thereto. Then catalytic reduction was effected under atmospheric pressure in a hydrogen atmosphere at room temperature to thereby give 1.7 g (yield: 99%) of 7-(2-aminophenyl)benz[g]indole.

Subsequently, 20 ml of ethanol was added to 540 mg (2.1 mmol) of 7-(2-aminophenyl)benz[g]indole and 260 mg (2.5 mmol) of ethyl glyoxylate (polymeric) and the obtained mixture was heated under reflux for 8 hours. After distilling off the solvent, the residue was purified by silica gel column chromatography to thereby give 380 mg (yield: 53%) of the title compound.

$^1$H-NMR(CDCl$_3$) δ (ppm);1.64(t,J=7.1 Hz,3H),4.74(q, J=7.1 Hz,2H),7.63–7.77(m,3H),7.79(d,J=8.6 Hz,1H), 7.79–7.85(m,1H),8.06(dd,J=1.3,7.7 Hz,1H),8.35 (dd,J=0.7, 8.1 Hz,1H),8.45(dd,J=1.3,8.4 Hz,1H),8.54(d,J=8.6 Hz,1H), 8.79(dd,J=1.1,8.2 Hz,1H),10.98(br-s,1H)

Example 1

5-[2-(Dimethylamino)ethyl]-4H-benzo[c]pyrimido[5,6,1-jk]carbazole-4,6(5H)-dione hydrochloride

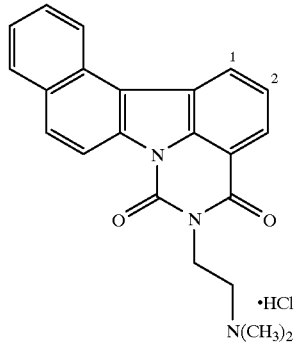

457 mg (10. 5mmol) of sodium hydride (55% oily) was added to a solution of 1.44 g of the compound of Production Example 3 in dimethylformamide (50 ml) at room temperature and the obtained mixture was stirred for 50 minutes. Then 1 ml (10.5 mmol) of ethyl chloroformate was added thereto at 0° C. and the obtained mixture was stirred at the same temperature for 2 hours and then at room temperature for 6 hours. After adding water, the precipitate was recovered by filtration, washed with water and dried. Then It was dissolved in a mixture of dichloromethane with methanol and the insoluble matters were filtered off. After concentrating, ethanol and conc. hydrochloric acid were successively added thereto. The hydrochloride thus formed was recovered by filtration and recrystallized from ethanol to thereby give 1.24 g of the title compound.

M.p.: 254–255° C. (recrystallized from ethanol). FAB mass spectrometry m/z: 358 ([M+H]$^+$). $^1$H-NMR(DMSO-d$_6$) δ (ppm); 2.90(d,J=5.5 Hz,6H),3.49 (q,J=5.5 Hz,2H),4.42 (t,J=5.5 Hz,2H),7.67(t,J=8.0 Hz,1H), 7.78(t,J=8.0 Hz,1H), 7.83(t,J=8.0 Hz,1H),8.14(d, J=8.0 Hz,1H),8.19(d,J=8.0 Hz,1H),8.23(d,J=8.8 Hz,1H), 8.62(d,J=8.0 Hz,1H),8.86(d, J=8.0 Hz,1H),9.02(d, J=8.0 Hz,1H),9.70(br-s,1H). Elemental analysis: as C$_{22}$H$_{19}$N$_3$O$_2$.HCl.H$_2$O

|  | C | H | N |
|---|---|---|---|
| calcd. | 64.15 | 5.38 | 10.20 |
| found | 64.38 | 5.05 | 10.22 |

Example 2

11-Acetyl-5-[2-(dimethylamino)ethyl]-4H-benzo[c]pyrimido[5,6,1-jk]carbazole-4,6(5H)-dione hydrochloride

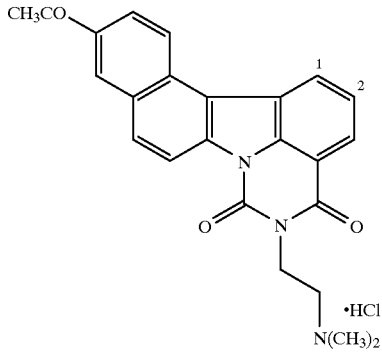

13.2 mg (0.549 mmol) of sodium hydride was added to a solution of 105 mg (0.282 mmol) of the compound of Production Example 5 in dimethylformamide (2.5 ml) at 0° C. and the obtained mixture was stirred at the same temperature for 1 hour and 10 minutes and then at room temperature for 1 hour. Then 53.6 μl (0.564 mmol) of ethyl chloroformate was added thereto at 0° C. and the obtained mixture was stirred at the same temperature for 1 hour and 20 minutes. After extracting by adding water and chloroform, the organic layer was taken up, dried over sodium sulfate and concentrated. The residue was purified by silica gel column chromatography and converted into its hydrochloride by using 1 N hydrochloric acid (ethanol) to thereby give 106 mg of the title compound.

M.p.: being colored from about 240° C. on and decomposed at about 250–254° C. FAB mass spectrometry m/z: 400 ([M+H]$^+$). $^{1H}$-NMR(DMSO-d$_6$) δ (ppm); 2.78(s,3H), 2.92(s,6H),3.48– 3.54(m,2H),4.44(t,J=5.6 Hz,2H),7.80(t,J= 7.5 Hz,1H), 8.16(d,J=7.5 Hz,1H),8.24(dd,J=2.3,9.4 Hz,1H), 8.40(d, J=8.9 Hz,1H),8.68(d,J=8.9 Hz,1H),8.87–8.91(m, 2H), 9.01(d,J=7.5 Hz,1H),9.88(br-s,1H). Elemental analysis: as $C_{24}H_{21}N_3O_3 \cdot HCl \cdot H_2O$

|  | C | H | N |
|---|---|---|---|
| Calcd. | 63.50 | 5.33 | 9.26 |
| found | 63.42 | 5.04 | 9.16 |

Example 3

5-[2-(Dimethylamino)ethyl]-11-(1-hydroxyethyl)-4H-benzo[c]pyrimido[5,6,1-jk]carbazole-4,6(5H)-dione hydrochloride

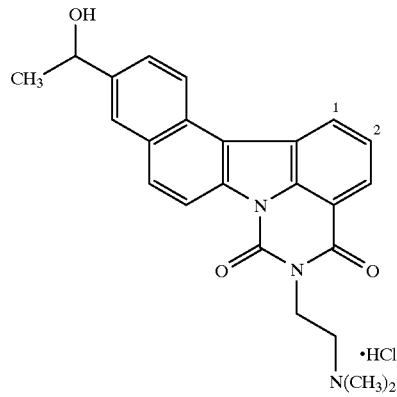

21 μl (0.168 mmol) of a borane/pyridine complex (about 8 M) was added to a suspension of 84 mg (0.211 mmol) of a compound prepared by converting the compound of Example 2 into its free base in acetic acid (1.5 ml) and the obtained mixture was stirred at 70° C. for 3 hours. Then it was acidified by adding 1 N hydrochloric acid thereto at room temperature, stirred for 1 minute and neutralized with a saturated aqueous solution of sodium bicarbonate. Next, it was extracted by adding thereto a mixture of dichloromethane with ethanol. The organic layer was taken up, washed with water, dried over sodium sulfate and concentrated. The residue was purified by preparative thin layer chromatography and converted into its hydrochloride by using 1 N hydrochloric acid to thereby give 44 mg of the title compound.

M.p.; 247~248° C. (decomposition) (recrystallized from ethanol). FAB MASS SPECTROMETRY m/z:402 ([M+H]$^+$). $^1$H-NMR(DMSO-d$_6$) δ (ppm); 1.50(d,J=5.0 Hz,3H), 2.92 (s,6H),3.49(t,J=5.7 Hz, 2H),4.43(t,J=5.7 Hz,2H), 4.95–5.05(m,1H),5.45(d,J=4.2 Hz,1H),7.77(t,J=8.4 Hz,1H), 7.84(d,J=8.4 Hz,1H),8.08–8.15(m,2H),8.21(d,J=8.4 Hz, 1H),8.59(dd,J=1.4,8.4 Hz,1H),8.81(d,J=8.4 Hz,1H),8.99(d, J=7.6 Hz,1H),9.90(br-s,1H). Elemental analysis: as $C_{24}H_{24}N_3O_3Cl$

|  | C | H | N |
|---|---|---|---|
| Calcd. | 65.82 | 5.52 | 9.60 |
| found | 65.49 | 5.53 | 9.49 |

Example 4

12,13-Dihydro-5-[2-(dimethylamino)ethyl]-4H-benzo[c]pyrimido[5,6,1-jk]carbazole-4,6,10(5H,11H)-trione hydrochloride

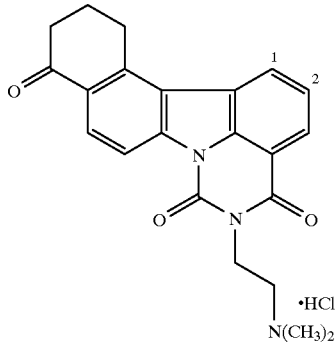

A solution of 4.9 g (14 mmol) of the compound of Production Example 8 in dimethylformamide (70 ml) was dropped into a suspension of 0.9 g (37.5 mmol) of sodium hydride in dimethylformamide (30 ml) at room temperature and the obtained mixture was stirred at the same temperature for 2 hours. Then 2.5 g (23 mmol) of ethyl chloroformate was added thereto under ice-cooling and stirring. 15 minutes thereafter, ethyl acetate was added thereto and the obtained mixture was washed successively with dilute aqueous ammonia and an aqueous solution of sodium chloride and dried over magnesium sulfate. After concentrating, methanol was added thereto and crystals were recovered by filtration. Then these crystals were suspended in methanol and acidified by adding 1 N hydrochloric acid thereto under stirring. After stirring at room temperature and concentrating, ethanol was added thereto and the precipitate thus formed was recovered by filtration to thereby give 4.3 g of the title compound.

M.p.: being colored from about 250° C. on, gradually decomposed from about 260° C. on and rapidly decomposed at about 273–275° C. FAB MASS SPECTROMETRY m/z:376 ([M+H]$^+$). $^1$H-NMR(DMSO-d$_6$) δ (ppm); 2.22–2.36(m,2H),2.72–2.80(m,2H),2.92(s,6H), 3.44–3.54(m,2H),3.54–3.60(m,2H),4.38–4.46(m,2H),7.75(t,J=7.6 Hz,1H),8.17 (dd,J=0.8,7.6 Hz,1H),8.25(d,J=8.8 Hz,1H), 8.41(d,J=8.8H z,1H),8.61(dd,J=0.8,7.6 Hz,1H),9.52(br-s, 1H). Elemental analysis: as $C_{22}H_{21}N_3O_3 \cdot HCl \cdot 1H_2O$

|  | C | H | N |
|---|---|---|---|
| Calcd. | 61.47 | 5.63 | 9.77 |
| found | 61.47 | 5.57 | 9.77 |

Example 5

5-[2-(Dimethylamino)ethyl]-10-hydroxy-10,11,12,13-tetrahydro-4H-benzo[c]pyrimido[5,6,1-jk]carbazole-4,6(5H)-dione

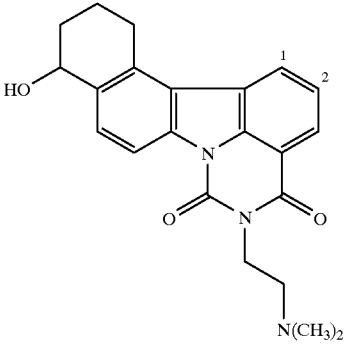

0.5 g (1.2 mmol) of the compound of Example 4 was dissolved in a mixture of water (50 ml) with methanol (25 ml) and 1.2 ml of 1 N hydrochloric acid was added thereto. Next, hydrogenation was effected in the presence of palladium-carbon under a hydrogen pressure of about 4.5 kg/cm$^2$. After confirming the completion of the reaction by thin layer chromatography, the catalyst was filtered off and the residue was concentrated to about 2/3. After adding 50 ml of water and 5 ml of conc. aqueous ammonia thereto, the obtained mixture was extracted with ethyl acetate. The organic layer was taken up, washed with an aqueous solution of sodium chloride, dried over magnesium sulfate and concentrated. The residue was purified by silica gel column chromatography to thereby give 0.35 g of the title compound.

FAB MASS SPECTROMETRY m/z:378 ([M+H]$^+$). $^1$H-NMR(CDCl$_3$) δ (ppm); 1.92–2.30(m,4H),2.37(s,6H), 2.70(t,J=6.8 Hz,2H),3.06–3.32(m,2H),4.32(t,J=6.8 Hz, 2H), 4.95(br-t,J=4.8 Hz,1H),7.52(t,J=7.6 Hz,1H),7.67 (d,J=8.4 Hz,1H),8.09(dd,J=0.8,7.6 Hz,1H),8.15(dd, J=0.8,7.6 Hz, 1H),8.33(d,J=8.4 Hz,1H). Elemental analysis: as $C_{22}H_{23}N_3O_3 \cdot 1H_2O$

|  | C | H | N |
|---|---|---|---|
| Calcd. | 66.82 | 6.37 | 10.63 |
| found | 67.10 | 6.03 | 10.34 |

Example 6

(+)-5-[2-(Dimethylamino)ethyl]-10-hydroxy-10,11,12,13-tetrahydro-4H-benzo[c]pyrimido[5,6,1-jk]carbazole-4,6(5H)-dione

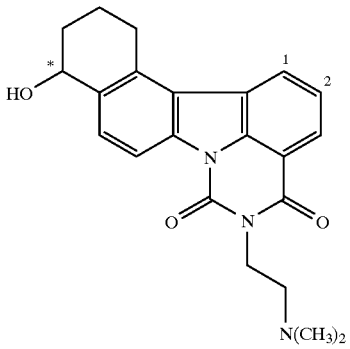

The compound of Example 5 was resolved with an optical resolution column [Chiralcel OD, mfd. by Daicel; eluted with n-hexane/2-propanol (7:3–6:4)]. The fraction eluted earlier was concentrated to dryness to thereby give the title compound.

M.p.; 160–162° C. FAB MASS SPECTROMETRY m/z:378 ([M+H]$^+$). $^1$H-NMR(CDCl$_3$) δ (ppm); 1.90–2.30 (m,4H),2.43(s,6H), 2.77(t,J=6.4 Hz,2H),3.04–3.31(m,2H), 4.34(t,J=6.8 Hz, 2H),4.95(br-t,J=4.8 Hz,1H),7.51(t,J=7.6 Hz,1H),7.68 (d,J=8.4 Hz,1H),8.08(d,J=7.6 Hz,1H),8.13(d, J=7.6 Hz, 1H),8.32(d,J=8.4 Hz,1H). Elemental analysis: as $C_{22}H_{23}N_3O_3 \cdot 0.75H_2O$

|  | C | H | N |
|---|---|---|---|
| Calcd. | 67.59 | 6.32 | 10.75 |
| found | 67.34 | 5.93 | 10.48 |

Angle of rotation $[a]_D^{27}$: +9.8° (C=1.0, CHCl$_3$).

Example 7

11,12-Dihydro-5-[2-(dimethylamino)ethyl]-4H,10H-ccylopenta[c]pyrimido[5,6,1-jk]carbazole-4,6,10(5H)-trione hydrochloride

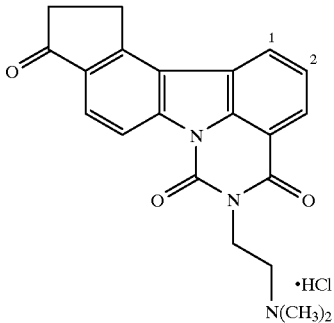

The title compound was obtained from the compound of Production Example 10 by the same method as the one of Example 2.

M.p.: being colored from about 255° C. on and gradually decomposed from about 265° C. on. FAB MASS SPECTROMETRY m/z:362 ([M+H]$^+$). $^1$H-NMR(DMSO-d$_6$) δ (ppm); 2.83–2.94(m,8H),3.45 (br-s,2H),3.64(br-t,J=6.0 Hz,2H),4.42(br-t,J=6.0 Hz, 2H),7.79(t,J=7.6 Hz,1H),7.97(d, J=8.4 Hz,1H),8.19(dd, J=0.8,7.6 Hz,1H),8.49(d,J=8.4 Hz,1H),8.55(dd,J=0.8, 7.6 Hz,1H), 9.44(br-s,1H). Elemental analysis: as $C_{21}H_{19}N_3O_3 \cdot HCl \cdot 0.75H_2O$

|  | C | H | N |
|---|---|---|---|
| Calcd. | 61.31 | 5.27 | 10.21 |
| found | 61.17 | 5.04 | 10.16 |

Example 8

8-[2-(Dimethylamino)ethyl]-7H-furo[3,2-c]pyrimido[5,6,1-jk]carbazole-3,7,9(2H,8H)-trione hydrochloride

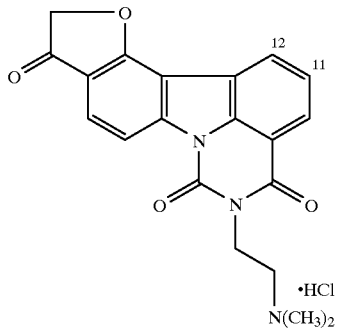

590 mg (2.2 mmol) of the compound of Production Example 15 was dissolved in dimethylformamide (20 ml). After adding 720 mg (4.4 mmol) of N,N'-carbonyldiimidazole thereto, the obtained mixture was stirred at room temperature for 30 minutes. Then 0.97 ml (8.8 mmol) of N,N-dimethylethylenediamine was further added thereto and the obtained mixture was stirred overnight followed by concentration. Water was added to the residue and the obtained mixture was extracted with a mixture of ethyl acetate with tetrahydrofuran. The organic layer was taken up, washed successively with a saturated aqueous solution of sodium bicarbonate and water and dried over magnesium sulfate. After concentrating, the residue was purified by silica gel column chromatography to thereby give 250 mg of 2,3-dihydro-N-[2-(dimethylamino)ethyl]-3-oxo-6H-furo[3,2-c]carbazole-7-carboxamide. This product was dissolved in dimethylformamide (10 ml). After adding 60 mg (1.5 mmol) of sodium hydride (oily 60%) thereto, the mixture was stirred in a nitrogen atmosphere for 30 minutes. After adding 0.145 ml (1.5 mmol) of ethyl chlorformate thereto under ice-cooling, the obtained mixture was stirred for 30 minutes and then acidified by adding 1 N hydrochloric acid thereto. After concentrating, a saturated aqueous solution of sodium bicarbonate was added thereto and the obtained mixture was extracted with a mixture of ethyl acetate with tetrahydrofuran. The organic layer was taken up, washed with water, dried over magnesium sulfate, concentrated and purified by silica gel column chromatography. Then it was suspended in ethanol (20 ml). After adding thereto 1 ml of 1 N hydrochloric acid and stirring, crystals were recovered by filtration to thereby give 175 ml of the title compound.

M.p.: being colored from about 240° C. on and decomposed at about 270–273° C. FAB MASS SPECTROMETRY m/z:364 ([M+H]$^+$). $^1$H-NMR(DMSO-d$_6$) δ (ppm); 2.89(br-s,6H),3.42–3.50(m,2H),4.39–4.45(m,2H),5.14(s,2H),7.78(t, J=7.7 Hz,1H),7.95(d,J=8.4 Hz,1H),8.17(dd,J=0.8,7.7 Hz,1H),8.22(d,J=8.4 Hz.,1H),8.43(dd,J=0.8,7.7 Hz,1H), 9.62(br-s,1H). Elemental analysis: as C$_{20}$H$_{17}$N$_3$O$_4$.HCl.0.15H$_2$O

|  | C | H | N |
|---|---|---|---|
| Calcd. | 59.68 | 4.58 | 10.44 |
| found | 59.64 | 4.49 | 10.33 |

Example 9

2,3-Dihydro-8-[2-(dimethylamino)ethyl]-3-hydroxy-7H-furo[3,2-c]pyrimido[5,6,1-jk]carbazole-7,9(8H)-dione

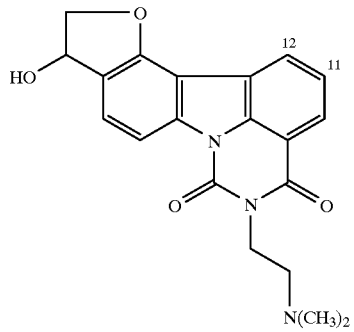

105.5 mg (0.29 mmol) of the compound of Example 8 was dissolved in acetic acid (1 ml). Then 36 μl of an 8 M borane/pyridine complex was added thereto under stirring at room temperature. The obtained mixture was stirred for 4.5 hours. After adding 30 μl of an 8 M borane/pyridine complex thereto, the obtained mixture was further stirred overnight and concentrated. Then it was extracted by adding thereto water, a saturated aqueous solution of sodium hydrogencarbonate and chloroform. The organic layer was dried over anhydrous sodium sulfate and concentrated. The residue was purified by silica gel column chromatography. The product thus obtained was recrystallized from ethanol/diisopropyl ether to thereby give 22.6 mg of the title compound.

$^1$H-NMR(DMSO-d$_6$) δ (ppm); 2.24(s,6H),2.56(t,J=6.8 Hz,2H),4.15(t,J=6.8 Hz,2H), 4.56(dd,J=2.8,10.0 Hz,1H), 4.84(dd,J=6.8,10.0 Hz,1H), 5.43–5.49(m,1H),5.80(d,J=5.6 Hz,1H),7.61–7.67(m,2H), 7.97(d,J=8.4 Hz,1H),8.02(dd,J= 0.8,7.6 Hz,1H),8.22(dd,J=0.8,7.6 Hz,1H)

Example 10

12,13-Dihydro-5-[2-(methylamino)ethyl]-4H-benzo[c]pyrimido[5,6,1-jk]carbazole-4,6,10(5H,11H)-trione hydrochloride

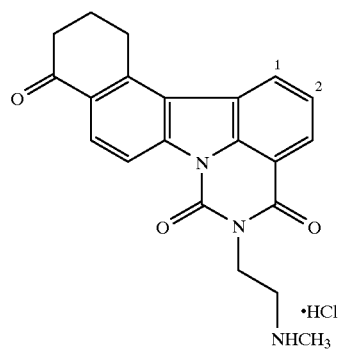

0.23 g (0.57 mmol) of the compound of Production Example 17 and 95 mg (0.1 mmol) of tris (triphenylphosphine)rhodium chloride (95 mg; 0.1 mmol) were dissolved in 20 ml of a mixture of acetonitrile with water (84:16). Then the obtained mixture was heated in a nitrogen atmosphere to thereby distill off the solvent, while dropping a mixture of acetonitrile with water (84:16) thereinto so as to maintain the volume of the mixture at a constant level. After continuing this operation for about 3 hours, the disappearance of the starting compounds was confirmed by thin layer chromatography. Then the reaction mixture was concentrated to about 1/4 and extracted with ethyl acetate. The organic layer was taken up, washed successively with dilute aqueous ammonia and an aqueous solution of sodium chloride, dried over magnesium sulfate and concentrated. The residue was purified by preparative thin layer chromatography and then converted into its hydrochloride by the same method as that of Example 4 to thereby give 0.1 g of the title compound.

M.p.: being colored from about 250° C. on, gradually decomposed from about 260° C. on and rapidly decomposed at about 267–269° C. FAB MASS SPECTROMETRY m/z:362 ([M+H]$^+$). $^1$H-NMR(DMSO-d$_6$.D$_2$O) δ (ppm); 2.24–2.34(m,2H),2.59 (s,3H),2.76(br-t,J=6.0 Hz,2H),3.31 (br-t,J=5.2 Hz,2H), 3.56(br-t,J=6.0 Hz,2H),4.36(br-t,J=5.2 Hz,2H),7.75 (t,J=8.0 Hz,1H),8.16(d,J=8.0 Hz,1H),8.24(d,J= 8.8 Hz, 1H),8.39(d,J=8.8 Hz,1H),8.59(d,J=8.0 Hz,1H). Elemental analysis: as C$_{21}$H$_{19}$N$_3$O$_3$.HCl.0.2H$_2$O

|  | C | H | N |
|---|---|---|---|
| calcd. | 62.83 | 5.12 | 10.47 |
| found | 62.78 | 5.09 | 10.36 |

Example 11

12,13-Dihydro-5-[2-(1-pyrrolidinyl)ethyl]-4H-benzo[c]pyrimido[5,6,1-jk]carbazole-4,6,10(5H,11H)-trione hydrochloride

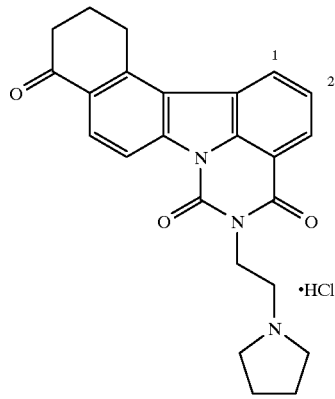

The title compound was obtained by reacting the compound of Production Example 7 with 1-(2-aminoethyl) pyrrolidine by the same methods as those of Production Example 8 and Example 4.

M.p.: being colored from about 235° C. on and gradually decomposed from about 260° C. on. FAB MASS SPECTROMETRY m/z:402 ([M+H]$^+$). $^1$H-NMR(DMSO-d$_6$) δ (ppm); 1.86(br-s, 2H),2.01 (br-s,2H),2.23–2.32(m,2H), 2.71–2.79(m,2H),3.15 (br-s,2H),3.46–3.74(br-t+m,J=6.0 Hz,4H+2H),4.40 (br-t,J=5.2 Hz,2H),7.73(t,J=8.0 Hz,1H), 8.15(d,J=8.0 Hz, 1H),8.23(d,J=8.8 Hz,1H),8.39(d,J=8.8 Hz,1H),8.57 (d,J=8.0 Hz,1H),10.10(br-s,1H). Elemental analysis: as C$_{24}$H$_{23}$N$_3$O$_3$.HCl.1.5H$_2$O

|  | C | H | N |
| --- | --- | --- | --- |
| calcd. | 62.00 | 5.85 | 9.04 |
| found | 62.27 | 5.49 | 9.03 |

Example 12

5-[2-(1-Pyrrolidinyl)ethyl]-4H-benzo[c]pyrimido[5,6,1-jk]carbazole-4,6(5H)-dione hydrochloride

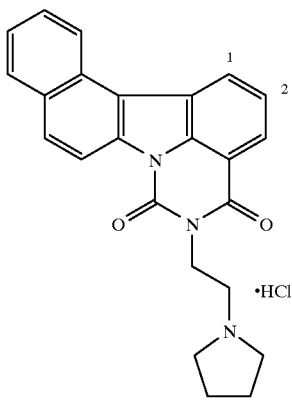

The title compound was obtained by reacting the compound of Production Example 2 with 1-(2-aminoethyl) pyrrolidine by the same methods as those of Production Example 3 and Example 1.

FAB MASS SPECTROMETRY m/z:384 ([M+H]$^+$). $^1$H-NMR(DMSO-d$_6$) δ (ppm); 1.78–1.92 (m, 2H) 1.94–2.06 (m,2H),3.08–3.22(m,2H),3.56(t,J=5.6 Hz,2H),3.60–3.70 (m,2H),4.41(t,J=5.6 Hz,2H),7.66(t,J=7.6 Hz,1H),7.75(t, J=8.0 Hz,1H),7.81(t,J=8.0 Hz,1H),8.11(d,J=7.6 Hz,1H), 8.18(d,J=8.0 Hz,1H),8.21(d,J=9.2 Hz,1H),8.60(d, J=9.2 Hz,1H),8.83(d,J=8.0 Hz,1H),8.98(d,J=7.6 Hz,1H), 10.29 (br-s,1H). Elemental analysis: as C$_{24}$H$_{21}$N$_3$O$_3$.HCl.H$_2$O

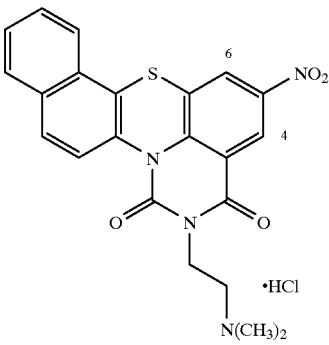

Example 13

2-[2-(Dimethylamino)ethyl]-5-nitro-1H-benzo[c]pyrimido [5,6,1-kl]phenothiazine-1,3(2H)-dione hydrochloride

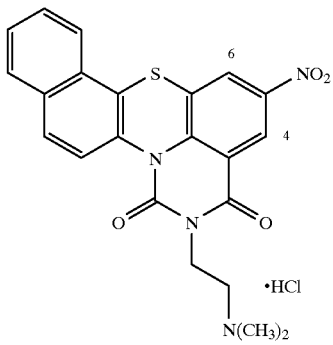

A solution of 200 mg (0.49 mmol) of the compound of Production Example 23 in tetrahydrofuran (15 ml) was stirred at room temperature and 0.5 ml of triethylamine and 200 μl (2.09 mmol) of ethyl chloroformate were successively added thereto. After stirring at room temperature overnight, the reaction mixture was concentrated and extracted by adding thereto water, a saturated aqueous solution of sodium hydrogencarbonate and dichloromethane. The organic layer was washed successively with water and a saturated aqueous solution of sodium chloride, dried over anhydrous magnesium sulfate and concentrated to dryness. The residue was recrystallized from ethanol to thereby give 104 mg of the free base of the title compound. Next, this product was suspended in methanol and conc. hydrochloric acid was added thereto under stirring. Then the obtained mixture was concentrated to dryness to thereby give the title compound.

$^1$H-NMR(DMSO-d$_6$) δ (ppm); 2.90(s,6H),3.49(br-s,2H), 4.38 (t,J=5.6 Hz,2H),7.66(t,J=7.6 Hz,1H),7.73(t,J=7.6 Hz, 1H),7.82(d,J=9.2 Hz,1H),7.96(d,J=8.8 Hz,1H),8.03(d, J=8.0 Hz,1H),8.09(d,J=8.4 Hz,1H),8.49–8.52(m,1H), 8.59–8.62 (m,1H),9.72(br-s,1H)

Example 14

2-[2-(Dimethylamino)ethyl]-1H-pyrimido[5,6,1-jk]thieno[3,2-a]carbazole-1,3(2H)-dione hydrochloride

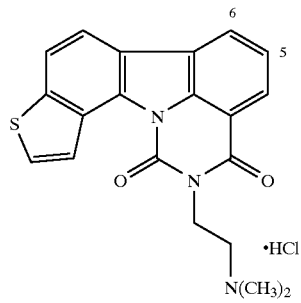

The title compound was obtained by starting with 4-oxo-4,5,6,7-tetrahydro-benzo[b]thiophene and 2-hydrazinobenzoic acid hydrochloride and repeating the procedures of Production Examples 1, 2 and 3 and Example 2.

$^1$H-NMR(DMSO-d$_6$) δ (ppm); 2.92(br-s,6H),3.44–3.57 (m,2H),4.44–4.51(m,2H),7.74(t,J=7.6 Hz,1H),7.98(d, J=5.6 Hz,1H),8.13(dd,J=0.8,7.6 Hz,1H),8.26(d,J=8.4 Hz,1H),8.36 (d,J=8.4 Hz,1H),8.65(dd,J=0.8,7.6 Hz,1H),8.84(d, J=5.6 Hz,1H),9.53(br-s,1H)

Example 15

2,3-Dihydro-9-[2-(dimethylamino)ethyl]-4H,8H-pyrano[3,2-c]pyrimido[5,6,1-jk]carbazole-4,8,10(9H)-trione hydrochloride

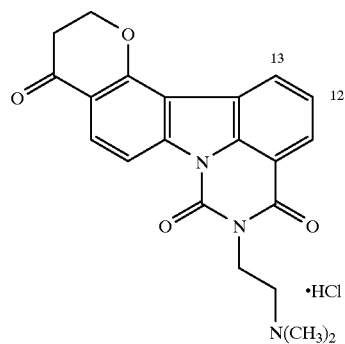

The title compound was obtained by the same procedure as that of Example 2.

FAB MASS SPECTROMETRY m/z:378 ([M+H]$^+$). $^1$H-NMR(DMSO-d$_6$) δ (ppm); 2.88(s,6H),2.99(t,J=6.4HZ, 2H),3.46(br-s,2H),4.40(br-t,J=5.6 Hz,2H),4.89(t, J=6.4 Hz,2H),7.73(t,J=7.6 Hz,1H),8.06(d,J=8.4 Hz,1H), 8.09(d,J=8.4 Hz,1H),8.12(d,J=7.6 Hz,1H)),8.42(d, J=7.6 Hz,1H),9.68 (br-s,1H). Elemental analysis: as C$_{21}$H$_{19}$N$_3$O$_4$.HCl.1.25H$_2$O

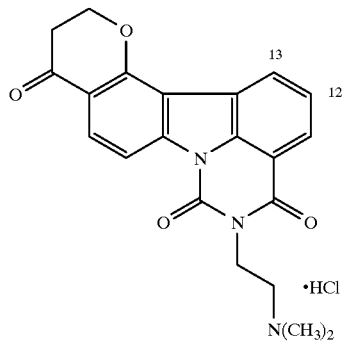

Example 16

9-[2-(Dimethylamino)ethyl]-4H,8H-pyrano[3,2-c]pyrimido [5,6,1-jk]carbazole-4,8,10(9H)-trione hydrochloride

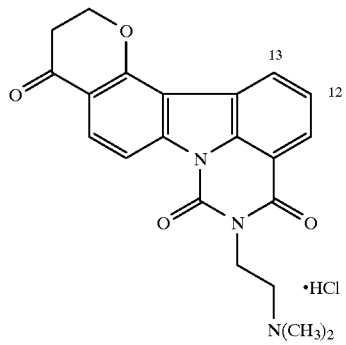

The title compound was obtained by the same procedure as that of Example 2.

FAB MASS SPECTROMETRY m/z:376 ((M+H]$^+$). $^1$H-NMR(DMSO-d$_6$) δ (ppm); 2.89(s,6H),3.46(br-s,2H), 4.43 (br-t,J=5.6 Hz,2H),6.55(d,J=6.0 Hz,1H),7.83(t, J=7.6 Hz,1H),8.23(dd,J=0.8,7.6 Hz,1H),8.34(d,J=8.8 Hz,1H),8.48 (d,J=8.8 Hz,1H),8.54(d,J=6.0 Hz,1H)),8.65(dd,J=0.8,7.6 Hz,1H),9.52(br-s,1H)

Example 17

2-[2-(Dimethylamino)ethyl]-1H-furo[3,2-a]pyrimido[5,6,1-jk]carbazole-1,3(2H)-dione hydrochloride

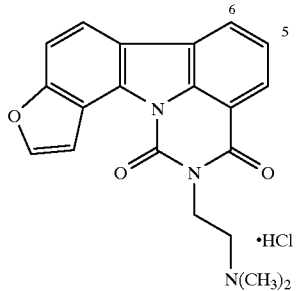

The title compound was obtained by starting with 4-oxo-4,5,6,7-tetrahydrobenzo[b]furane and 2-hydrazinobenzoic acid hydrochloride and repeating the procedures of Production Examples 1, 2 and 3 and Example 2.

$^1$H-NMR(DMSO-d$_6$) δ (ppm); 2.91(br-s,6H),3.40–3.55(m,2H),4.41–4.51(m,2H),7.72(t,J=7.6 Hz,1H),7.83(d, J=2.0 Hz,1H),7.88(d,J=8.4 Hz,1H),8.09(d,J=7.6 Hz,1H), 8.20(d, J=2.0 Hz,1H),8.32(d,J=8.4 Hz,1H)),8.61(d, J=7.6 Hz,1H), 9.46(br-s,1H)

Example 18

2-[2-(Dimethylamino)ethyl]-1H-benzo[a]pyrimido[5,6,1-jk]carbazole-1,3(2H)-dione hydrochloride

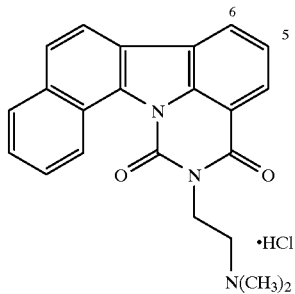

The title compound was obtained by starting with α-tetralone and 2-hydrazinobenzoic acid hydrochloride and repeating the procedures of Production Examples 1, 2 and 3 and Example 2.

$^1$H-NMR(DMSO-d$_6$) δ (ppm); 2.89(s,6H),3.49(br-s,2H), 4.49(t,J=5.5 Hz,2H),7.64–7.71(m,2H),7.74(t, J=8.0 Hz,1H), 8.11–8.18(m,3H),8.44(d,J=8.3 Hz,1H), 8.66(d,J=8.0 Hz,1H),9.59(br-s,1H),9.76(d,J=8.3 Hz,1H). Elemental analysis: as C$_{22}$H$_{19}$N$_3$O$_2$.HCl.0.2H$_2$O

|  | C | H | N |
|---|---|---|---|
| Calcd. | 66.48 | 5.17 | 10.57 |
| found | 66.47 | 5.20 | 10.51 |

Example 19

5-[3-(Dimethylamino)propyl]-4H-benzo[c]pyrimido[5,6,1-jk]carbazole-4,6(5H)-dione hydrochloride

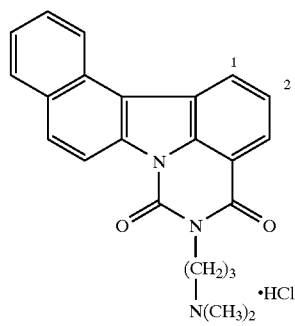

The title compound was obtained by reacting the compound of Production Example 2 with N,N-dimethyl-1,3-propanediamine in the same manner as those of Production Example 3 and Example 1.

FAB MASS SPECTROMETRY m/z:372 ([M+H]$^+$). $^1$H-NMR(DMSO-d$_6$) δ (ppm); 2.03–2.13(m,2H),2.74(s, 6H), 3.19(t,J=8.0 Hz,2H),4.12(t,J=6.0 Hz,2H),7.65(t, J=7.2 Hz,1H),7.75(t,J=8.0 Hz,1H),7.81(t,J=7.6 Hz,1H), 8.10(d,J= 7.6 Hz,1H),8.16(d,J=8.0 Hz,1H),8.19(d, J=9.6 Hz,1H),8.58 (d,J=9.6 Hz,1H),8.80(t,J=8.4 Hz,1H), 8.94(d,J=8.0 Hz,1H), 9.69(br-s,1H). Elemental analysis: as C$_{23}$H$_{21}$N$_3$O$_2$.HCl.0.3H$_2$O

|  | C | H | N |
|---|---|---|---|
| Calcd. | 66.84 | 5.51 | 10.17 |
| found | 66.75 | 5.45 | 10.03 |

Example 20

2-[2-(Dimethylamino)ethyl]-1H,11H-indeno[1',2':4,5]pyrrolo[3,2,1-ij]quinazoline-1,3(2H)-dione hydrochloride

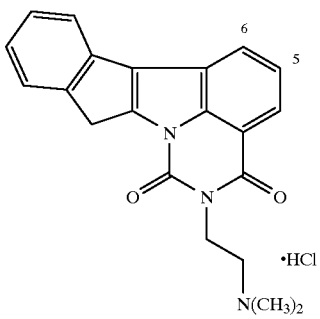

The title compound was obtained by starting with 2-indanone and 2-hydrazinobenzoic acid hydrochloride and repeating the procedures of Production Examples 1 and 3 and Example 2.

$^1$H-NMR(CD$_3$OD) δ (ppm); 3.02(s,6H),3.53(t,J=5.8 Hz,2H),4.10(s,2H),4.50(t, J=5.8 Hz,2H),7.28(dt,J=1.2,7.6 Hz,1H),7.41(dt,J=1.0, 7.6 Hz,1H),7.56–7.59(m,1H),7.62(t, J=7.7 Hz,1H),7.76–7.79(m,1H),8.02(dd,J=0.8,7.7 Hz,1H), 8.25(dd,J=0.8, 7.7 Hz,1H)

Example 21

7-[2-(Dimethylamino)ethyl]-6H,14H-benzo[a]pyrimido[5,6,1-de]acridine-6,8,14(7H)-trione hydrochloride

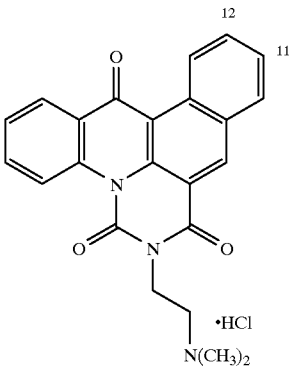

The title compound was obtained by the same procedure as that of Example 2.

¹H-NMR(DMSO-d₆) δ (ppm); 2.91(br-s,6H),3.50–3.56(m,2H),4.49(t,J=5.7 Hz,2H),7.64–7.69(m,1H),7.77–7.82(m,1H),7.87–7.92(m,1H),7.98–8.03(m,1H),8.37–8.40(m,1H),8.43–8.46(m,1H),8.63(dd,J=0.5,8.8 Hz,1H), 9.26(s,1H),9.81(dd,J=0.7,8.6 Hz,1H),10.04(br-s,1H)

Example 22

5-[2-(Dimethylamino)ethyl]-11-methoxy-4H-benzo[c]pyrimido [5,6,1-jk]carbazole-4,6(5H)-dione hydrochloride

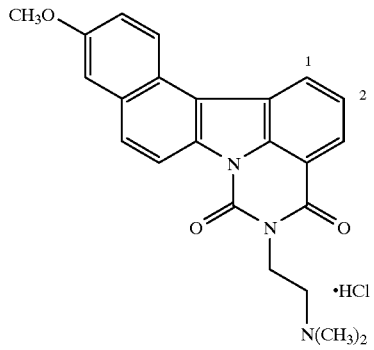

The title compound was obtained by starting with 6-methoxy-β-tetralone and 2-hydrazinobenzoic acid hydrochloride and repeating the procedures of Production Examples 24 and 3 and Example 2.

¹H-NMR(DMSO-d₆) δ (ppm); 2.93(d,J=4.6 Hz,6H), 3.47–3.54(m,2H),3.94(s,3H),4.39–4.45(m,2H),7.46(dd, J=2.2,9.0 Hz,1H),7.62(d,J=2.2 Hz,1H),7.78(t,J=8.4 Hz, 1H), 8.14(d,J=8.4 Hz,1H),8.16(d,J=9.0 Hz,1H),8.59(d, J=9.0 Hz,1H),8.78(d,J=9.0 Hz,1H),9.01(d,J=8.4 Hz,1H), 9.16(br-s,1H). Elemental analysis: as $C_{23}H_{21}N_3O_3 \cdot HCl \cdot 1.5H_2O$

|       | C     | H    | N    |
|-------|-------|------|------|
| Calcd. | 61.26 | 5.59 | 9.32 |
| found | 61.08 | 5.46 | 9.40 |

Example 23

5-[2-(Dimethylamino)ethyl]-10-methoxy-4H-benzo[c]pyrimido[5,6,1-jk]carbazole-4,6(5H)-dione hydrochloride

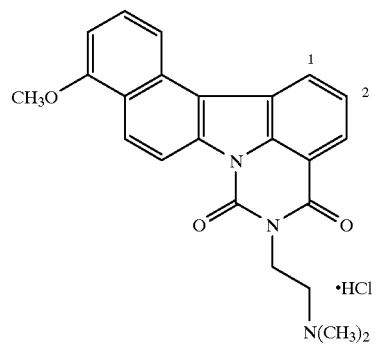

The title compound was obtained by starting with 5-methoxy-β-tetralone and 2-hydrazinobenzoic acid hydrochloride and repeating the procedures of Production Examples 1, 2 and 3 and Example 2.

¹H-NMR(DMSO-d₆) δ (ppm); 2.89(s,6H),3.44–3.51(m, 2H), 4.04(s,3H),4.40(t,J=6.2 Hz,2H),7.12(d,J=8.2 Hz,1H), 7.72(t,J=8.5 Hz,1H),7.73(dt,J=3.4,8.2 Hz,1H),8.09(d, J=8.5 Hz,1H),8.32(d,J=8.5 Hz,1H),8.41(d,J=8.5 Hz,1H), 8.52(dd, J=1.0,8.5 Hz,1H),8.88(d,J=8.5 Hz,1H),9.93(br-s,1H). Elemental analysis: as $C_{23}H_{21}N_3O_3 \cdot HCl \cdot 1.3H_2O$

|       | C     | H    | N    |
|-------|-------|------|------|
| Calcd. | 61.76 | 5.54 | 9.40 |
| found | 61.89 | 5.32 | 9.45 |

Example 24

2-[2-(Dimethylamino)ethyl]-1H-benzo[b]pyrimido[1,6,5-lm]-4-azacarbazole-1,3(2H)-dione dihydrochloride

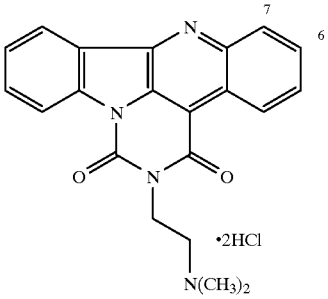

The title compound was obtained by the same procedure as that of Example 2.

¹H-NMR(DMSO-d₆) δ (ppm); 2.90(s,6H),3.47–3.55(m, 2H), 4.48(t,J=6.3 Hz,2H),7.67(t,J=7.8 Hz,1H),7.86–7.95 (m,3H),8.36–8.44(m,3H),9.24–9.29(m,1H),10.41 (br-s, 1H)

Example 25

1,2-Dihydro-9-[2-(dimethylamino)ethyl]-4H,8H-pyrano[3,4-c]pyrimido[5,6,1-jk]carbazole-4,8,10 (9H)-trione hydrochloride

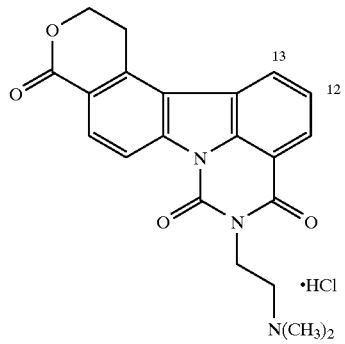

The title compound was obtained by the same procedure as that of Example 2.

¹H-NMR(DMSO-d₆) δ (ppm); 2.89(s,6H),3.47(t,J=6.0 Hz,2H),3.64(t,J=6.0 Hz,2H), 4.38(t,J=6.0 Hz,2H),4.68(t,J= 6.0 Hz,2H),7.73(t, J=7.6 Hz,1H),8.15(t,J=7.6 Hz,1H),8.27 (d,J=8.8 Hz,1H), 8.44(d,J=8.8 Hz,1H),8.55(d,J=7.6 Hz,1H), 9.82(br-s,1H)

Example 26

5-[2-(Dimethylamino)ethyl]-12-methoxy-4H-benzo[c]pyrimido [5,6,1-jk]carbazole-4,6(5H)-dione hydrochloride

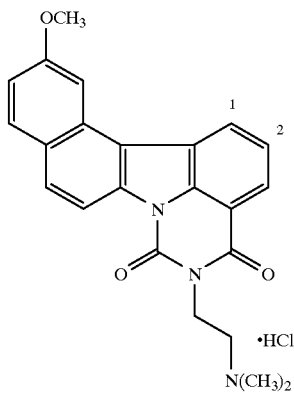

The title compound was obtained by starting with 7-methoxy-β-tetralone and 2-hydrazinobenzoic acid hydrochloride and repeating the procedures of Production Examples 1, 2 and 3 and Example 2.

$^1$H-NMR(DMSO-d$_6$) δ (ppm); 2.85(br-s,6H),3.35–3.46 (m,2H),4.08(s,3H),4.39(br-s,2H),7.32(dd,J=2.2, 8.8 Hz,1H),7.79(t,J=7.8 Hz,1H),7.99(d,J=1.7 Hz,1H), 8.09–8.19(m,3H),8.48(d,J=8.8 Hz,1H),8.97 (d,J=7.8 Hz,1H),9.25(br-s,1H)

Example 27

2-[2-(Dimethylamino)ethyl]-5-nitro-1H-benzo[b]pyrimido [5,6,1-kl]phenoxazine-1,3(2H)-dione hydrochloride

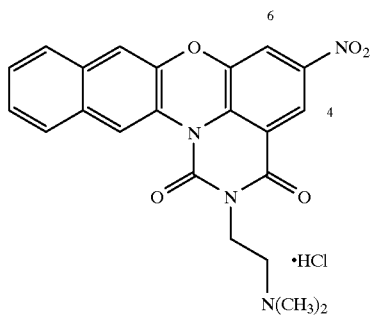

304 mg (1.91 mmol) of 3-amino-2-naphthol, 477 mg (1.81 mmol) of methyl 2-chloro-3,5-dinitrobenzoate and 178 mg (2.17 mmol) of sodium acetate were suspended in a mixture of water (5 ml) with ethanol (10 ml) and heated under reflux for 7 hours. After adding 3 ml of a 2 N aqueous solution of sodium hydroxide thereto, the reaction mixture was heated under reflux for additional 2.5 hours and then brought back to room temperature. After adding 10 ml of 1 N hydrochloric acid thereto, the precipitate thus formed was recovered by filtration and washed successively with water, 1 N hydrochloric acid and ethanol to thereby give 430 mg of 3-nitro-12H-benzo[b]phenoxazine-1 -carboxylic acid. Then this product was treated by the same methods as those of Production Example 23 and Example 13 to thereby give the title compound.

$^1$H-NMR(DMSO-d$_6$) δ (ppm); 2.89(s,6H),3.45(t,J=5.2 Hz, 2H),4.40(t,J=5.2 Hz,2H),7.47(t,J=8.0 Hz,1H),7.52(t,J= 8.0 Hz,1H),7.69(s,1H),7.86(d,J=6.8 Hz,1H),7.88(d, J=8.0 Hz,1H),8.19(d,J=2.4 Hz,1H),8.34(d,J=2.4HZ,1H), 9.05(s, 1H),9.82(br-s,1H)

Example 28

2-Chloro-5-[2-(dimethylamino)ethyl]-4H-benzo[c]pyrimido [5,6,1-jk]carbazole-4,6(5H)-dione hydrochloride

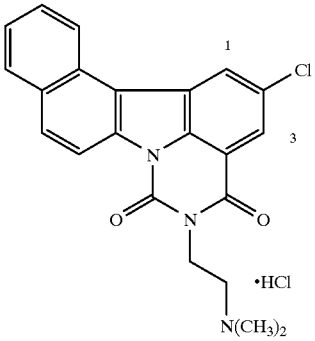

The title compound was obtained by starting with β-tetralone and 5-chloro-2-hydrazinobenzoic acid hydrochloride and repeating the procedures of Production Examples 1, 2 and 3 and Example 2.

$^1$H-NMR(DMSO-d$_6$) δ (ppm); 2.89(br-s,6H),3.39– 3.53 (m,2H),4.38–4.48(m,2H),7.68–7.75(m,1H),7.81–7.89(m, 1H),8.13(d,J=1.6 Hz,1H),8.22(d,J=8.4 Hz,1H), 8.31(d,J=8.8 Hz,1H),8.63(d,J=8.8 Hz,1H),8.94(d, J=8.4 Hz,1H),9.14(d, J=1.6 Hz,1H),9.46(br-s,1H). Elemental analysis: as $C_{22}H_{18}N_3O_2Cl\cdot HCl\cdot 1.75H_2O$

|        | C     | H    | N    |
|--------|-------|------|------|
| Calcd. | 57.46 | 4.93 | 9.14 |
| found  | 57.65 | 4.57 | 8.76 |

Example 29

9-[2-(Dimethylamino)ethyl]-8H-pyrido[4,3-c]pyrimido[5,6,1-jk]carbazole-1,8,10(2H,9H)-trione hydrochloride

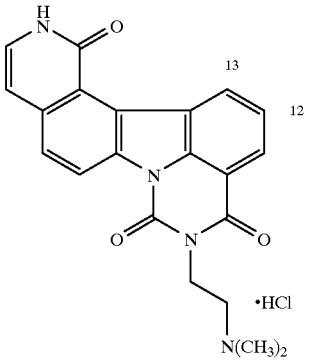

The title compound was obtained by saponifying an ester of the compound of Production Example 20 and then repeating the procedures of Production Example 3 and Example 2.

¹H-NMR(DMSO-d₆) δ (ppm); 2.90(br-s,6H),3.43–3.53 (m,2H),4.40–4.46(m,2H),6.80–6.83(m,1H),7.34–7.38 (m,1H),7.73(t,J=7.9 Hz,1H),8.01(d,J=8.9 Hz,1H),8.18 (dd, J=0.9,7.9 Hz,1H),8.89(d,J=8.9 Hz,1H),9.52 (br-s,1H),9.91 (dd,J=0.9,7.9 Hz,1H),11.67–11.71(m,1H). Elemental analysis: as $C_{21}H_{18}N_4O_3 \cdot HCl \cdot 1.3H_2O$

|  | C | H | N |
|---|---|---|---|
| Calcd. | 58.08 | 5.01 | 12.90 |
| found | 57.94 | 4.78 | 12.72 |

Example 30

5-[2-(Dimethylamino)ethyl]-4H-quino[4',3'-4,5] pyrrolo [3,2,1-ij]quinazoline-4,6(5H)-dione dihydrochloride

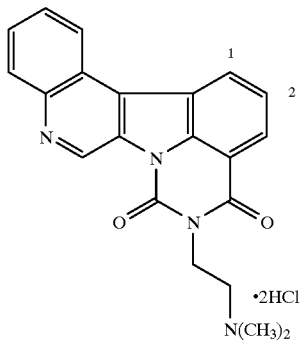

The title compound was obtained by the same method as the one of Production Example 2.

FAB MASS SPECTROMETRY m/z;359 ([M+H]⁺).
¹H-NMR(DMSO-d₆+D₂O ) δ (ppm); 2.94 (s, 6H), 3.54 (br-t,J=5.6 Hz,2H),4.47(br-t,J=5.6 Hz,2H), 7.89(t,J=7.6 Hz,1H),7.91–7.99(m,2H),8.30–8.37 (m,2H),8.89–8.95(m, 1H),9.16(d,J=7.6 Hz,1H), 9.97(s,1H). Elemental analysis: as $C_{21}H_{18}N_4O_2 \cdot 2HCl \cdot 0.5H_2O$

|  | C | H | N |
|---|---|---|---|
| Calcd. | 57.28 | 4.81 | 12.72 |
| found | 57.28 | 4.97 | 12.60 |

Example 31

5-Amino-2-[2-(dimethylamino)ethyl]-1H-benzo[b] pyrimido [5,6,1-kl]phenoxazine-1,3(2H)-dione dihydrochloride

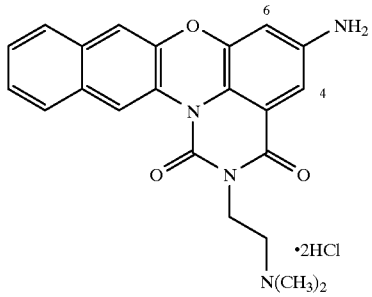

268 mg (0.641 mmol) of the free base of the compound of Example 27 was dissolved in acetic acid (10 ml) and 10% palladium-carbon was added thereto. Then catalytic reduction was effected at room temperature in a hydrogen atmosphere. After filtering off the palladium-carbon through celite, the filtrate was concentrated. Next, water and a saturated aqueous solution of sodium hydrogencarbonate were added thereto and the obtained mixture was stirred at room temperature. The precipitate was recovered by filtration, washed with water and suspended in methanol. After adding conc. hydrochloric acid thereto, the obtained mixture was stirred at room temperature. Thus it turned into a homogeneous solution and then a precipitate was formed. The precipitate was recovered by filtration to thereby give 179 mg of the title compound.

¹H-NMR(DMSO-d₆) δ (ppm); 2.89(s,6H),3.43(t,J=5.6 Hz,2H),4.34(t,J=5.6 Hz,2H), 6.76(s,1H),6.96(s,1H), 7.38–7.48(m,2H),7.59(s,1H), 7.79(d,J=8.0 Hz,1H),7.81(d, J=8.0 Hz,1H),9.15(s,1H), 9.65(br-s,1H)

Example 32

5-[2-(Dimethylamino)ethyl]-13-methoxy-4H-benzo [c]pyrimido [5,6,1-jk]carbazole-4,6(5H)-dione hydrochloride

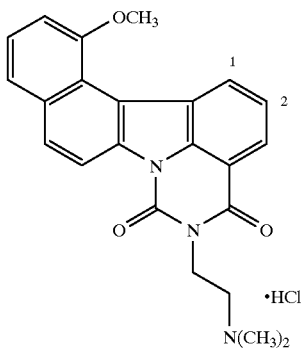

The title compound was obtained by starting with 8-methoxy-β-tetralone and 2-hydrazinobenzoic acid hydrochloride and repeating the procedures of Production Examples 1, 2 and 3 and Example 2.

¹H-NMR(DMSO-d₆) δ (ppm); 2.91(br-s,6H),3.40–3.53 (m,2H),4.23(s,3H),4.40–4.49(m,2H),7.33(d,J=7.6 Hz, 1H), 7.61(t,J=8.0 Hz,1H),7.72–7.79(m,2H),8.15(d, J=8.0 Hz,1H),8.23(d,J=8.8 Hz,1H),8.82(d,J=8.8 Hz,1H), 9.09(d, J=8.0 Hz,1H),9.35(br-s,1H). Elemental analysis: $C_{23}H_{21}N_3O_3 \cdot HCl \cdot 0.65H_2O$

|       | C     | H    | N    |
|-------|-------|------|------|
| Calcd.| 63.42 | 5.39 | 9.65 |
| found | 63.31 | 5.14 | 9.68 |

Example 33

9-[2-(Dimethylamino)ethyl]-8H-pyrido[4,3-c]pyrimido[5,6,1-jk]carbazole-8,10(9H)-dione dihydrochloride

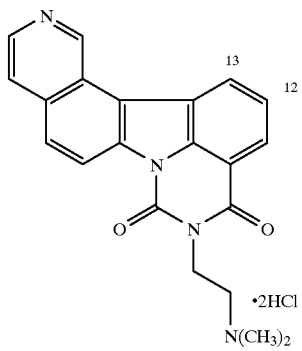

300 mg (1.1 mmol) of the compound of Production Example 21 was dissolved in a mixture of tetrahydrofuran (10 ml) with methanol (10 ml). After adding 5 ml of 1 N sodium hydroxide thereto, the obtained mixture was heated under reflux for 1 hour. Then 7H-pyrido[4,3-c]carbazole-8-carboxylic acid isolated in a conventional manner was dissolved in dimethylformamide (40 ml) and 360 mg (2.2 mmol) of N,N'-carbonyldiimidazole was added thereto. After stirring at room temperature for 30 minutes, 0.48 ml (4.4 mmol) of N,N-dimethylethylenediamine was added thereto and the obtained mixture was stirred overnight. After concentrating, it was extracted by adding water and ethyl acetate. The organic layer was taken up, washed successively with a saturated aqueous solution of sodium bicarbonate and water and dried over magnesium sulfate. After concentrating, the residue was purified by silica gel column chromatography to thereby give 250 mg of N-[2-(dimethylamino)ethyl]-7H-pyrido[4,3-c]carbazole-8-carboxamide. Then this product was reacted and treated in the same manner as the one of Example 2 to thereby give 110 mg of the title compound.

M.p.: being colored from about 270° C. on and decomposed at 279° C. $^1$H-NMR(DMSO-$d_6$) δ (ppm); 2.89–2.93 (m, 6H) 3.49–3.54 (m,2H),4.46(t,J=6.0 Hz,2H),7.85(t,J=7.6 Hz,1H),8.25(d, J=7.6 Hz,1H),8.40–8.44(m,2H),8.79(d,J= 6.4 Hz,1H),9.04 (d,J=9.2 Hz,1H),9.23(d,J=7.6 Hz,1H),10.10 (br-s,1H), 10.44 (s,1H). Elemental analysis: $C_{21}H_{18}N_4O_2 \cdot 2HCl \cdot 2H_2O$

|       | C     | H    | N     |
|-------|-------|------|-------|
| Calcd.| 53.97 | 5.18 | 11.99 |
| Found | 54.11 | 4.99 | 11.99 |

Example 34

5-[4-(Dimethylamino)butyl]-4H-benzo[c]pyrimido[5,6,1-jk]carbazole-4,6(5H)-dione hydrochloride

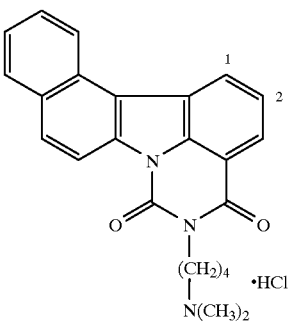

The title compound was obtained by reacting the compound of Production Example 2 with N,N-dimethyl-1,4-butanediamine by the same methods as those of Production Example 3 and Example 1.

FAB MASS SPECTROMETRY m/z;386 ([M+H]$^+$). $^1$H-NMR(DMSO-$d_6$) δ (ppm); 1.68–1.85(m,4H),2.74(s, 6H), 3.09(br-t,J=6.4 Hz,2H),4.10(br-t,J=6.4 Hz,2H), 7.64–7.70(m,1H),7.75(t,J=7.6 Hz,1H),7.79–7.85(m,1H), 8.11 (d,J=7.6 Hz,1H),8.16–8.24(m,2H),8.62(d,J=8.8 Hz,1H), 8.83(d,J=8.4 Hz,1H),8.97(d,J=7.6 Hz,1H),9.99(br-s,1H). Elemental analysis: as $C_{24}H_{23}N_3O_2 \cdot HCl \cdot 0.5H_2O$

|       | C     | H    | N    |
|-------|-------|------|------|
| Calcd.| 66.89 | 5.85 | 9.75 |
| found | 66.54 | 5.71 | 9.66 |

Example 35

11-Cyano-5-[2-(dimethylamino)ethyl]-4H-benzo[c]pyrimido [5,6,1-jk]carbazole-4,6(5H)-dione hydrochloride

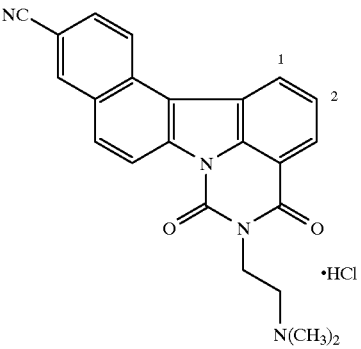

The title compound was obtained in the same manner as the one of Example 2.

¹H-NMR(DMSO-d₆) δ (ppm); 2.93(s,6H),3.48–3.55(m, 2H), 4.46(t,J=5.6 Hz,2H),7.83(t,J=8.2 Hz,1H),8.10(dd,J= 1.3, 8.9 Hz,1H),8.21(d,J=8.2 Hz,1H),8.38(d,J=8.9 Hz,1H), 8.79(d,J=8.9 Hz,1H),8.88(d,J=1.3 Hz,1H),9.04(d, J=8.9 Hz,1H),9.10(d,J=8.2 Hz,1H)

Example 36

9-[2-(Dimethylamino)ethyl]-8H-pyrido[2,3-c]pyrimido[5,6,1-jk]carbazole-8,10(9H)-dione dihydrochloride

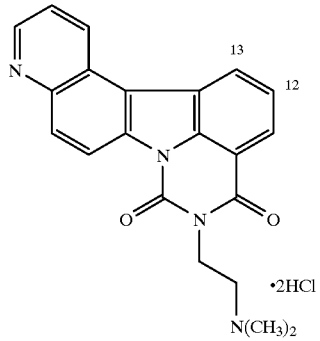

The title compound was obtained in the same manner as the one of Example 2.

¹H-NMR(DMSO-d₆) δ (ppm); 2.92(s,3H),2.93(s,3H), 3.46–3.58(m,2H),4.41–4.51(m,2H),7.82(t,J=8.0 Hz,1H), 7.92 (dd,J=4.8,8.4 Hz,1H),8.21(d,J=8.0 Hz,1H),8.40(d, J=9.2 Hz,1H),8.92(d,J=9.2 Hz,1H),9.10(d,J=8.0 Hz,1H), 9.14(dd,J=0.8,4.8 Hz,1H),9.47(dd,J=0.8,8.4 Hz,1H), 9.86 (br-s,1H). Elemental analysis: as C₂₁H₁₈N₄O₂·2HCl·0.75H₂O

|  | C | H | N |
|---|---|---|---|
| Calcd. | 56.70 | 4.87 | 12.59 |
| found | 56.78 | 4.82 | 12.36 |

Example 37

5-[2-(Dimethylamino)ethyl]-2-nitro-4H-benzo[c]pyrimido [5,6,1-jk]carbazole-4,6(5H)-dione hydrochloride

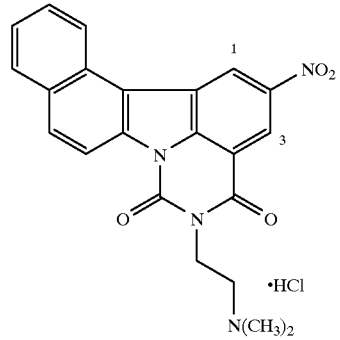

The title compound was obtained by starting with β-tetralone and 5-nitro-2-hydrazinobenzoic acid and repeating the procedures of Production Examples 1, 2 and 3 and Example 2.

H-NMR(DMSO-d₆) δ (ppm); 289(s,6H),3.44–3.52(m, 2H), 4.45(t,J=5.2 Hz, 2H), 7.73(t,J=8.1 Hz,1H),7.90(t, J=8.1 Hz,1H),8.23(d,J=8.1 Hz,1H),8.35(d,J=9.2 Hz,1H), 8.63(d,J=9.2 Hz,1H),8.80(d,J=1.8 Hz,1H),8.94(d, J=8.1 Hz,1H),9.64 (d,J=1.8 Hz,1H),9.75(br-s,1H)

Example 38

5-[2-(Dimethylamino)ethyl]-2-methyl-4H-benzo[c]pyrimido [5,6,1-jk]carbazole-4,6(5H)-dione hydrochloride

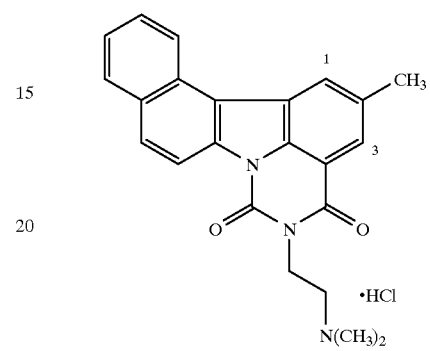

The title compound was obtained by starting with β-tetralone and 2-hydrazino-5-methylbenzoic acid hydrochloride and repeating the procedures of Production Examples 1, 2 and 3 and Example 2.

¹H-NMR(DMSO-d₆) δ (ppm); 2.71(s,3H),2.90(br-s,6H), 3.38–3.55(m,2H), 4.39–4.46(m,2H),7.66–7.72(m, 1H), 7.81–7.88(m,1H),7.97–8.00(m,1H),8.18–8.23 (m,1H), 8.22–8.27(m,1H),8.63(d,J=9.2 Hz,1H),8.88–8.95(m,2H). Elemental analysis: as C₂₃H₂₁N₃O₂·HCl·1.5H₂O

|  | C | H | N |
|---|---|---|---|
| Calcd. | 63.52 | 5.79 | 9.66 |
| Found | 63.63 | 5.48 | 9.70 |

Example 39

1,2-Dihydro-9-[2-(dimethylamino)ethyl]-8H-pyrido[3,4-c]pyrimido[5,6,1-jk]carbazole-4,8,10(3H,9H)-trione hydrochloride

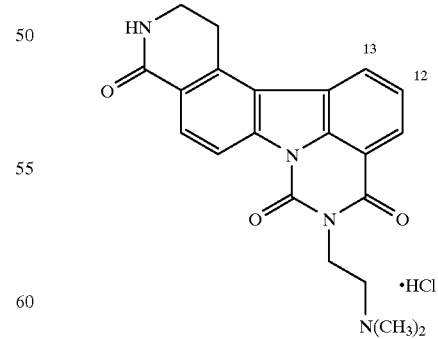

The title compound was obtained in the same manner as the one of Example 2.

¹H-NMR(DMSO-d₆) δ (ppm); 2.88(br-s,6H),3.37–3.52 (m,²H),3.50–3.64(m,4H),4.36–4.44(m,2H),7.73 (t,J=7.6

Hz,1H),8.11(br-s,1H),8.15(dd,J=0.8,7.6 Hz, 1H),8.22(d,J=8.4 Hz,1H),8.40(d,J=8.4 Hz,1H),8.57(dd, J=0.8,7.6 Hz,1H). Elemental analysis: as $C_{21}H_{20}N_4O_3 \cdot HCl \cdot H_2O$

|  | C | H | N |
|---|---|---|---|
| Calcd. | 58.54 | 5.38 | 13.00 |
| found | 58.50 | 5.49 | 12.77 |

Example 40

8-[2-(Dimethylamino)ethyl]-7H-1,3-dioxolo[4,5-c]pyrimido [5,6,1-jk]carbazole-7,9(8H)-dione hydrochloride

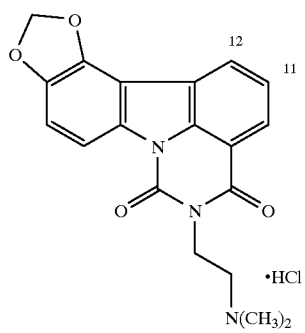

The title compound was obtained in the same manner as the one of Example 2.

$^1$H-NMR(DMSO-d$_6$) δ (ppm); 2.90(br-s,6H),3.42–3.49 (m,2H),4.36–4.42(m,2H),6.35(s,2H),7.29(d,J=8.4 Hz, 1H), 7.68(t,J=7.7 Hz,1H),7.89(d,J=8.4 Hz,1H),8.10(dd, J=0.8,7.7 Hz,1H),8.27(dd,J=0.8,7.7 Hz,1H),9.35 (br-s,1H)

Example 41

11-Bromo-5-[2-(dimethylamino)ethyl]-4H-benzo[c]pyrimido [5,6,1-jk]carbazole-4,6(5H)-dione hydrochloride

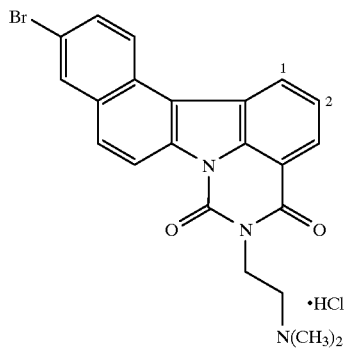

The title compound was obtained by starting with 6-bromo-β-tetralone and 2-hydrazinobenzoic acid hydrochloride and repeating the procedures of Production Examples 1, 2 and 3 and Example 2.

FAB MASS SPECTROMETRY m/z;436 ([M+H]$^+$),438 ([M+2+H]$^+$). $^1$H-NMR(DMSO-d$_6$) δ (ppm); 2.90(s,6H), 3.48(br-s,2H),4.42 (t,J=5.6 Hz,2H),7.77(t,J=7.6 Hz,1H), 7.89(dd,J=2.0, 8.8 Hz,1H),8.14(d,J=7.2 Hz,1H),8.20(d,J= 8.8 Hz,1H), 8.47(d,J=2.0 Hz,1H),8.63(d,J=8.8 Hz,1H),8.79 (d, J=9.2 Hz,1H),8.97(d,J=8.0 Hz,1H),9.74(br-s,1H). Elemental analysis: as $C_{22}H_{18}N_3O_2Br \cdot HCl \cdot 0.6H_2O$

|  | C | H | N |
|---|---|---|---|
| Calcd. | 54.64 | 4.21 | 8.69 |
| found | 54.36 | 3.94 | 8.56 |

Example 42

2-[2-(Dimethylamino)ethyl]-1H-benzo[b]pyrimido [5,6,1-jk]carbazole-1,3(2H)-dione hydrochloride

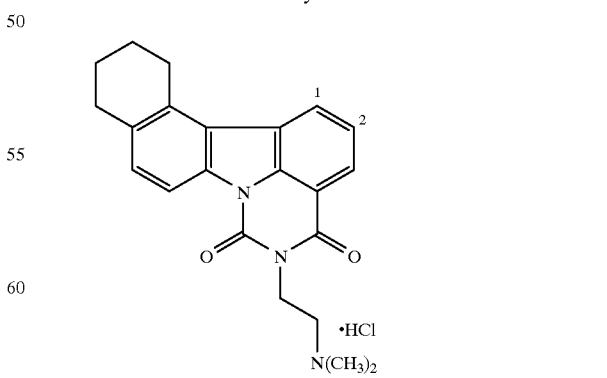

The title compound was obtained in the same manner as the one of Example 2.

FAB MASS SPECTROMETRY m/z;358 ([M+H]$^+$). $^1$H-NMR(DMSO-d$_6$) δ (ppm); 2.90(br-s,6H),3.39–3.53 (m,2H),4.37–4.48(m,2H),7.60–7.70(m,2H),7.73(t, J=7.6 Hz,1H),8.13(dd,J=0.8,7.6 Hz,1H),8.16–8.20 (m,1H), 8.21–8.26(m,1H),8.66(dd,J=0.8,7.6 Hz,1H),8.86 (s,1H), 8.93(s,1H). Elemental analysis: as $C_{22}H_{19}N_3O_2 \cdot HCl$

|  | C | H | N |
|---|---|---|---|
| Calcd. | 67.09 | 5.12 | 10.67 |
| found | 66.94 | 5.22 | 10.65 |

Example 43

5-[2-(Dimethylamino)ethyl]-10,11,12,13-tetrahydro-4H-benzo[b]pyrimido[5,6,1-jk]carbazole-4,6(5H)-dione hydrochloride The title compound was obtained from the compound of Example 4 in the same manner as the one of Example 5.

FAB MASS SPECTROMETRY m/z;362 ([M+H]$^+$).
$^1$H-NMR(DMSO-d$_6$) δ (ppm); 1,79–2.01(m,4H),2.89(s,6H), 2.90(br-t,J=6.0 Hz,2H),3.24(br-t,J=6.0 Hz,2H),3.46(br-t,J=5.6 Hz,2H),4.39(br-t,J=6.0 Hz,2H),7.38(d, J=8.8 Hz,1H),7.65(t,J=8.0 Hz,1H),8.06(d,J=8.0 Hz,1H), 8.13(d,J=8.8 Hz,1H),8.41(dd,J=0.8,8.0 Hz,1H),9.74 (br-s,1H). Elemental analysis: as C$_{22}$H$_{23}$N$_3$O$_2$.HCl.0.75H$_2$O

|  | C | H | N |
|---|---|---|---|
| Calcd. | 64.23 | 6.25 | 10.21 |
| found | 64.35 | 6.20 | 10.15 |

Example 44

12,13-Dihydro-11,11-dimethyl-5-[2-(dimethylamino)ethyl]-4H-benzo[c]pyrimido[5,6,1-jk]carbazole-4,6,10(5H,11H)-trione hydrochloride

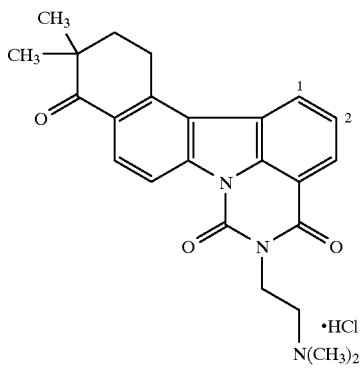

The title compound was obtained in the same manner as the one of Example 2.

$^1$H-NMR(DMSO-d$_6$) δ (ppm); 1.20(s,6H),2.13(t,J=6.1 Hz, 2H),2.88(s,6H),3.43(br-s,2H),3.52(t,J=6.1 Hz,2H), 4.38 (t,J=5.7 Hz,2H),7.71(t,J=7.4 Hz,1H), 8.11(d, J=7.4 Hz,1H), 8.20(d,J=8.8 Hz,1H),8.35(d,J=8.8 Hz,1H), 8.54(d,J=7.4 Hz,1H),10.08(br-s,1H). Elemental analysis: as C$_{24}$H$_{25}$N$_3$O$_3$.HCl.H$_2$O

|  | C | H | N |
|---|---|---|---|
| Calcd. | 62.94 | 6.16 | 9.18 |
| found | 63.06 | 6.27 | 9.14 |

Example 45

5-[2-(Dimethylamino)ethyl]-2-methoxy-4H-benzo[c]pyrimido [5,6,1-jk]carbazole-4,6(5H)-dione hydrochloride

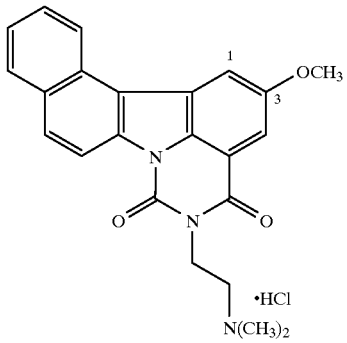

The title compound was obtained by starting with β-tetralone and 2-hydrazino-5-methoxybenzoic acid hydrochloride and repeating the procedures of Production Examples 1, 2 and 3 and Example 2.

$^1$H-NMR(DMSO-d$_6$) δ (ppm); 2.89(br-s,6H),3.40–3.52 (m, 2H),4.03(s,3H),4.40(t,J=6.0 Hz,2H),7.60(d,J=2.4 Hz, 1H),7.63–7.70(m,1H),7.76–7.85(m,1H),8.17(dd,J=0.4, 8.4 Hz,1H),8.21(d,J=8.8 Hz,1H),8.49(d,J=2.4 Hz,1H), 8.57(d, J=8.8 Hz,1H),8.84(dd,J=0.4,8.4 Hz,1H),9.57 (br-s,1H). Elemental analysis: as C$_{23}$H$_{21}$N$_3$O$_3$.HCl.H$_2$O

|  | C | H | N |
|---|---|---|---|
| Calcd. | 62.51 | 5.47 | 9.51 |
| Found | 62.44 | 5.22 | 9.48 |

Example 46

5-[2-(Dimethylamino)ethyl]-11-hydroxy-4H-benzo[c]pyrimido [5,6,1-jk]carbazole-4,6(5H)-dione hydrochloride

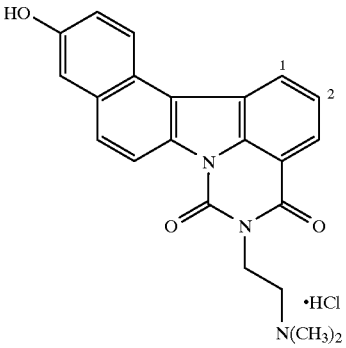

The compound of Example 22 was heated under reflux in 47% hydrobromic acid. Then the reaction mixture was catalytically reduced at room temperature with the use of palladium-carbon as the catalyst. The obtained product was converted into the hydrochloride by a conventional method to thereby give the title compound.

$^1$H-NMR(DMSO-d$_6$) δ (ppm); 2.92 (d, J=5.5 Hz, 6H) 3.48 (q,J=5.5 Hz,2H),4.41(t,J=5.5 Hz,2H),7.36–7.42(m, 2H), 7.73(t,J=8.1 Hz,1H),8.00(d,J=9.4 Hz,1H),8.11(d, J=8.1 Hz,1H),8.49(d,J=8.1 Hz,1H),8.71(d,J=9.4 Hz,1H), 8.94(d, J=8.1 Hz,1H),9.60(br-s,1H),10.01(br-s,1H)

Example 47

2-Amino-5-[2-(dimethylamino)ethyl]-4H-benzo[c]pyrimido [5,6,1-jk]carbazole-4,6(5H)-dione dihydrochloride

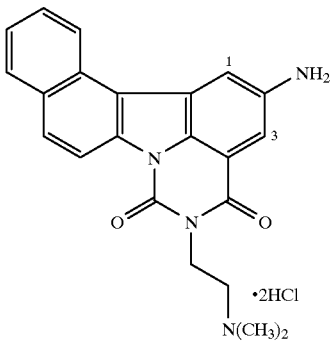

The compound of Example 37 was hydrogenated in the presence of a palladium-carbon catalyst at an ordinary temperature under atmospheric pressure to thereby give the title compound.

$^1$H-NMR(DMSO-d$_6$) δ (ppm); 2.89(d,J=4.1 Hz,6H), 3.44–3.51(m,$^2$H),4.40(t,J=5.8 Hz,2H),7.67(t,J=8.2 Hz,1H), 7.77(s,1H),7.84(t,J=8.2 Hz,1H),8.19(d,J=8.2 Hz,1H),8.22(d, J=9.3 Hz,1H),8.57(d,J=9.3 Hz,1H),8.61(d,J=8.2 Hz, 1H), 8.63(s,1H),9.94(br-s,1H)

Example 48

5-[2-(Dimethylamino)ethyl]-11-(4-methylbenzenesulfonamido)-4H-benzo[c]pyrimido [5,6,1-jk]carbazole-4,6(5H)-dione hydrochloride

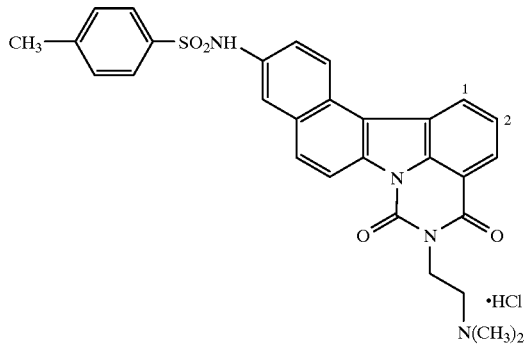

The compound of Production Example 24 was treated in the same manner as the one of Production Example 3 to thereby give N-[2-(dimethylamino)ethyl]-3-(4-methylbenzenesulfonamido)-7H-benzo[c]carbazole-8-carboxamide. Then this product was reacted with sodium hydride and ethyl chloroformate in dimethylformamide under ice-cooling to thereby give 5-[2-(dimethylamino) ethyl]-11-(N-etoxycarbonyl-4-methylbenzenesulfonamido)-4H-benzo[c]pyrimido[5,6,1-jk]carbazole-4,6(5H)-dione. Next, this product was treated with a 1 N aqueous solution of sodium hydroxide in a mixture of methanol with tetrahydrofuran (1:1) and then converted into the hydrochloride in a conventional manner followed by recrystallization from ethanol to thereby give the title compound.

$^1$H-NMR (DMSO-d$_6$) δ (ppm); 2.28 (s, 3H) 2.90(s, 6H), 3.48 (br-s,2H),4.41 (t,J=5.6 Hz,2H),7.33(d,J=9.2 Hz,2H), 7.60(d,J=8.8 Hz,1H),7.70–7.78(m,3H),7.82(s,1H),8.09 (d,J=9.2 Hz,1H),8.12(d,J=8.0 Hz,1H),8.54(d,J=8.4 Hz, 1H), 8.76(d,J=8.4 Hz,1H),8.94(d,J=8.4 Hz,1H),9.56 (br-s,1H), 10.68(s,1H)

Example 49

11-Amino-5-[2-(dimethylamino)ethyl]-4H-benzo[c]pyrimido [5,6,1-jk]carbazole-4,6(5H)-dione dihydrochloride

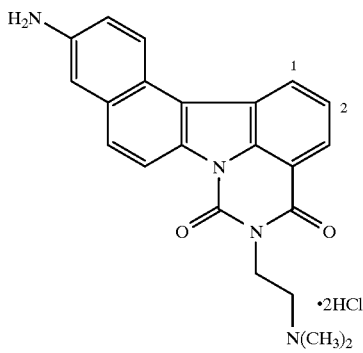

341 mg (0.648 mmol) of the free base of the compound of Example 48 and 419 mg (4.45 mmol) of phenol were heated under reflux in 47% hydrobromic acid (15 ml) for 9 hours and 30 minutes and then brought back to room temperature. The reaction mixture was then made basic by adding a saturated aqueous solution of sodium hydrogencarbonate thereto. Next, the obtained mixture was extracted by adding ethyl acetate and tetrahydrofuran thereto. The organic layer was washed successively with water and a saturated aqueous solution of sodium chloride and dried over anhydrous magnesium sulfate. The organic layer was concentrated and the obtained residue was recrystallized from ethanol to thereby give 141 mg of the free base of the title compound. Then this free base was converted into the hydrochloride in a conventional manner to thereby give the title compound.

(free base) $^1$H-NMR(DMSO-d$_6$) δ (ppm); 2.22(s,6H),2.55 (t,J=6.8 Hz,2H),4.14(t,J=6.8 Hz,2H),5.50–5.53(m,2H), 7.06 (d,J=2.0 Hz,1H),7.22(dd,J=2.4,9.2 Hz,1H),7.67(t, J=8.0 Hz,1H),7.79(d,J=9.2 Hz,1H),8.03(d,J=8.0 Hz,1H), 8.38(d, J=8.8 Hz,1H),8.52(d,J=9.2 Hz,1H),8.84(d, J=7.6 Hz,1H)

Example 50

11-Acetamido-5-[2-(dimethylamino)ethyl]-4H-benzo[c]pyrimido[5,6,1-jk]carbazole-4,6(5H)-dione hydrochloride

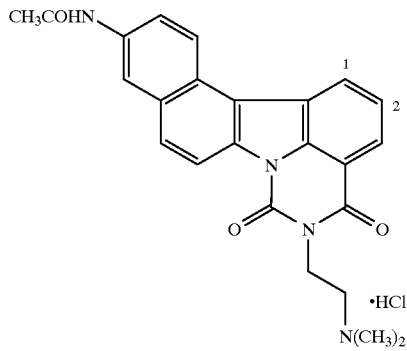

4 ml of triethylamine and 2 ml of acetic anhydride were successively added to a suspension of 141 mg (0.379 mmol) of the free base of the compound of Example 49 in dichloromethane (20 ml) under stirring at room temperature and stirring was continued for 16 hours. After concentrating, 30 ml of methanol was added to the residue. Next, the obtained mixture was made basic by adding an aqueous solution of sodium hydrogencarbonate thereto. The precipitate was recovered by filtration and washed with water. The solid matter thus obtained was suspended in ethanol and conc. hydrochloric acid was added thereto under stirring at room temperature. After further adding methanol and dichloromethane thereto, stirring was continued. After concentrating, ethanol was added thereto and the obtained mixture was heated under reflux and then brought back to room temperature. The precipitate was recovered by filtration to thereby give 148 mg of the title compound.

FAB MASS SPECTROMETRY m/z;415 ([M+H]$^+$).
$^1$H-NMR(DMSO-d$_6$) δ (ppm); 2.13(s,3H),2.90(s,3H),2.91 (s,3H),3.44–3.52(m,2H),4.42(t,J=5.6 Hz,2H),7.76(t, J=8.0 Hz,1H),7.89(dd,J=1.6,9.2 Hz,1H),8.06–8.14(m, 2H),8.52(d, J=1.6 Hz,1H),8.54(d,J=9.2 Hz,1H),8.79(d, J=8.8 Hz,1H), 8.98(d,J=8.0 Hz,1H),9.60(br-s,1H),10.35 (s,1H). Elemental analysis: as C$_{24}$H$_{22}$N$_4$O$_3$.HCl.0.6H$_2$O

|  | C | H | N |
| --- | --- | --- | --- |
| Calcd. | 62.43 | 5.28 | 12.13 |
| found | 62.54 | 5.03 | 11.82 |

Example 51

5-[2-[N-[2-(Dimethylamino)ethyl]-N-methylamino]ethyl]-4H-benzo[c]pyrimido[5,6,1-jk]carbazole-4,6(5H)-dione dihydrochloride

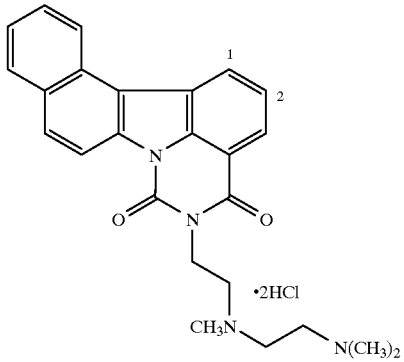

The title compound was obtained in the same manner as the one of Example 2.

(free base) $^1$H-NMR(CDCl$_3$) δ (ppm); 2.20(s,6H),2.42 (t,J=7.2 Hz,2H),2.45(s,3H),2.63(t,J=7.2 Hz,2H),2.81(t, J=7.2 Hz,2H),4.35(t,J=7.2 Hz,2H),7.59(t,J=7.8 Hz,1H), 7.64 (t,J=7.8 Hz,1H),7.74(t,J=7.8 Hz,1H),8.01(d, J=9.2 Hz,1H), 8.03(d,J=7.8 Hz,1H),8.14(d,J=7.8 Hz,1H), 8.56–8.61(m, 2H),8.66(d,J=9.2 Hz,1H). Elemental analysis: as C$_{25}$H$_{26}$N$_4$O$_2$.2HCl.0.8H$_2$O

|  | C | H | N |
| --- | --- | --- | --- |
| Calcd. | 59.83 | 5.78 | 11.17 |
| found | 59.83 | 6.02 | 11.16 |

Example 52

5-[2-[N-(2-(Hydroxyethyl)-N-methylamino]ethyl]-4H-benzo[c]pyrimido[5,6,1-jk]carbazole-4,6(5H)-dione hydrochloride

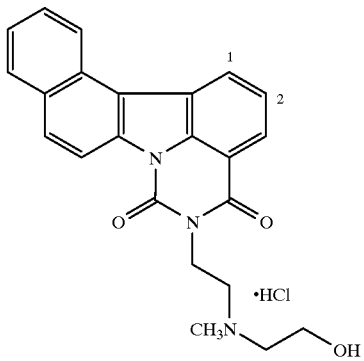

The title compound was obtained in the same manner as the one of Example 2.

$^1$H-NMR(DMSO-d$_6$) δ (ppm); 2.93(s,3H),3.14–3.67(m, 4H), 3.71–3.80(m,2H), 4.40–4.49(m,2H),5.33–5.39(m,1H), 7.64–7.70(m,1H),7.73–7.86(m,2H),8.10–8.26(m,3H), 8.59–8.65(m,1H),8.83–8.89(m,1H),9.00–9.04(m,1H), 9.60 (br-s,1H). Elemental analysis: as $C_{23}H_{21}N_3O_3 \cdot HCl \cdot 1.1H_2O$

|       | C     | H    | N    |
|-------|-------|------|------|
| Calcd.| 62.26 | 5.25 | 9.47 |
| Found | 62.08 | 5.55 | 9.47 |

Example 53

5-[2-[Dimethylamino)ethyl]-2-hydroxy-4H-benzo[c] pyrimido [5,6,1-jk]carbazole-4,6(5H)-dione hydrochloride

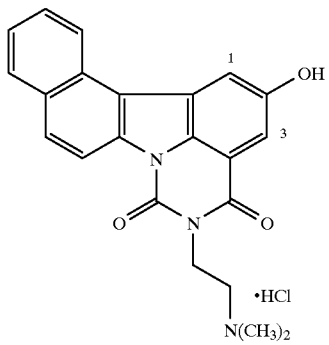

The title compound was obtained by treating the compound of Example 45 in the same manner as the one of Example 46.

$^1$H-NMR(DMSO-d$_6$) δ (ppm); 2.89(br-s,6H),3.39–3.54 (m,2H),4.32–4.46(m,2H),7.53–7.56(m,1H),7.65–7.71 (m,1H),7.81–7.87(m,1H),8.19(d,J=8.0 Hz,1H),8.23(d, J=8.8 Hz,1H),8.35–8.39(m,1H),8.60(d,J=8.8 Hz,1H),8.73 (d,J= 8.0 Hz,1H),9.29–9.39(br,1H),10.25(s,1H). Elemental analysis: as $C_{22}H_{19}N_3O_3 \cdot HCl \cdot H_2O$

|       | C     | H    | N    |
|-------|-------|------|------|
| Calcd.| 61.76 | 5.18 | 9.82 |
| found | 61.92 | 4.90 | 9.84 |

Example 54

2-[2-(Dimethylamino)ethyl]-9-methoxy-1H-benzo[a] pyrimido [5,6,1-jk]carbazole-1,3(2H)-dione hydrochloride

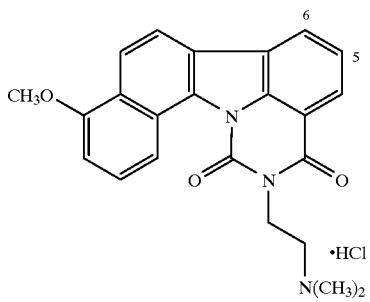

The title compound was obtained by starting with 5-methoxy-1-tetralone and 2-hydrazinobenzoic acid hydrochloride and repeating the procedure of Example 18.

$^1$H-NMR(DMSO-d$_6$) δ (ppm); 2.92(s6H),3.46–3.55(m, 2H), 4.02(s,3H),4.42–4.46(m,2H),7.16(d,J=7.1 Hz,1H),7.60 (t,J=7.1 Hz,1H),7.73(t,J=7.1 Hz,1H),8.12(d,J=7.1 Hz, 1H), 8.34–8.44(m,2H),8.63(d,J=7.1 Hz,1H),9.28(d, J=9.2 Hz,1H),9.78(br-s,1H)

Example 55

9-[2-(1-Pyrrolidinyl)ethyl]-8H-pyrido[2,3-c] pyrimido[5,6,1-jk]carbazole-8,10(9H)-dione dihydrochloride

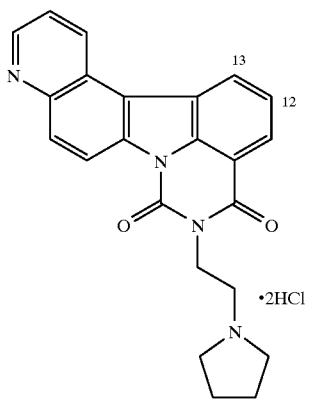

The title compound was obtained in the same manner as the one of Example 36.

$^1$H-NMR(DMSO-d$_6$+D$_2$O) δ (ppm); 1.84–1.94(m,2H), 2.01–2.13 (m,2H),3.13–3.25(m,2H),3.57–3.64(m,2H), 3.65–3.74(m, 2H),4.43–4.49(m,2H),7.85(t,J=7.6 Hz,1H), 7.94(dd, J=4.4,8.4 Hz,1H),8.23(d,J=7.6 Hz,1H),8.37(d,J= 9.2 Hz, 1H),8.92(d,J=9.2 Hz,1H),9.05(d,J=7.6 Hz,1H),9.12 (dd, J=1.6,4.4 Hz,1H),9.40–9.45(m,1H)

Example 56

9-[2-(Dimethylamino)ethyl]-13-fluoro-8H-pyrido[2, 3-c]pyrimido[5,6,1-jk]carbazole-8,10(9H)-dione dihydrochloride

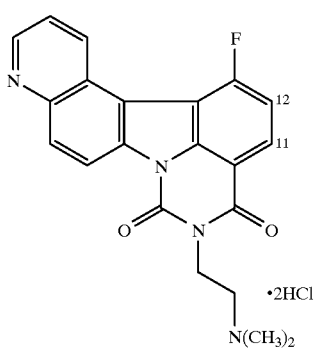

The title compound was obtained in the same manner as the one of Example 36.

$^1$H-NMR(DMSO-d$_6$) δ (ppm); 2.92(s,3H),2.93(s,3H), 3.47–3.55(m,2H),4.41–4.47(m,2H),7.69(dd,J=8.4,12.0 Hz, 1H),7.93(dd,J=4.4,8.4 Hz,1H),8.29(dd,J=4.4,8.4 Hz,1H), 8.45(d,J=9.2 Hz,1H),8.97(d,J=9.2 Hz,1H),9.10–9.14 (m,1H),9.25–9.31(m,1H)

Example 57

9-[2-(Dimethylamino)ethyl]-3-methyl-8H-pyrido[2,3-c]pyrimido[5,6,1-jk]carbazole-8,10(9H)-dione dihydrochloride

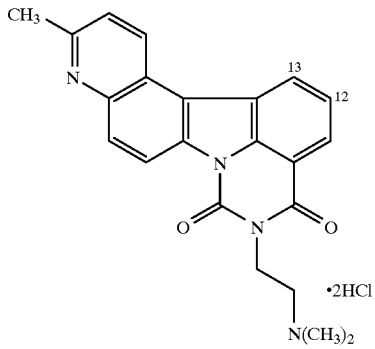

The title compound was obtained in the same manner as the one of Example 36.

$^1$H-NMR(DMSO-d$_6$+D$_2$O) δ (ppm); 2.93(s,3H),2.95(s,6H), 3.51–3.57(m,2H),4.44–4.50(m,2H),7.86(t,J=8.0 Hz,1H), 7.98(d,J=8.8 Hz,1H),8.25(d,J=8.0 Hz, 1H),8.39(d,J=9.2 Hz,1H),8.98(d,J=9.2 Hz,1H),9.09(d,J=8.0 Hz,1H), 9.55(d,J=8.8 Hz,1H)

Example 58

7-[2-(Dimethylamino)ethyl]-6H-benzo[c,i]pyrimido[1,6,5-lm]-β-carboline-6,8(7H)-dione

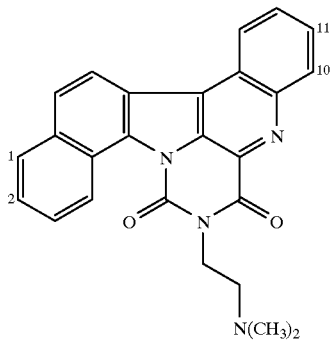

1.06 g (3.1 mmol) of the compound of Production Example 25 was dissolved in a mixture of methanol (20 ml) with tetrahydrofuran (20 ml). After adding a 1 N aqueous solution of sodium hydroxide (10 ml) thereto, the obtained mixture was heated under reflux for 1 hour and then allowed to cool. Next, a 1 N aqueous solution of hydrochloric acid (10 ml) was added thereto and the solvent was distilled off. To the residue was added N,N-dimethylformamide (50 ml). Further 770 mg (4 mmol) of 1-ethyl-3-(3-dimethylaminopropyl)carbodiimide hydrochloride, 540 mg (4 mmol) of 1-hydroxybenzotriazole and 0.4 ml (3.7 mmol) of N,N-dimethylethylenediamine were added thereto and the obtained mixture was stirred at room temperature overnight. Then an aqueous solution of sodium hydrogencarbonate was added thereto and the mixture was extracted with ethyl acetate. The organic layer was washed with water and a saturated aqueous solution of sodium chloride, dried over anhydrous magnesium sulfate and then concentrated. The precipitate thus formed was washed with ethanol and recovered by filtration to thereby give 660 mg of an intermediate (yield: 55%).

100 mg (0.26 mmol) of this intermediate was dissolved in N,N-dimethylformamide (20 ml) and 22mg (0.55 mmol) of sodium hydride (oily 60%) was added thereto under a nitrogen gas stream. After stirring the obtained mixture for 1 hour, 0.046 ml (0.6 mmol) of methyl chloroformate was added thereto at room temperature. Then the mixture was immediately acidified with 1 N hydrochloric acid and then made weakly alkaline with a saturated aqueous solution of sodium hydrogencarbonate followed by extraction with ethyl acetate. The organic layer was washed with a saturated aqueous solution of sodium chloride, dried over anhydrous magnesium sulfate and then concentrated to dryness. The residue was purified by silica gel column chromatography to thereby give 25 mg of the title compound (yield: 24%).

FAB MASS SPECTROMETRY m/z;409 ([M+H]$^+$).
$^1$H-NMR(CDCl$_3$) δ (ppm); 2.39(s,6H),2.80(t,J=6.7Hz,2H), 4.51(t,J=6.7 Hz,2H),7.66–7.78(m,2H),7.85–7.93(m,2H), 8.01–8.07(m,2H),8.51(d,J=8.6 Hz,1H),8.57–8.63(m,1H), 8.73–8.79(m,1H),9.74(dd,J=0.7,8.6 Hz,1H)

We claim:

1. A compound represented by the following general formula (I) or pharmacologically acceptable salts thereof:

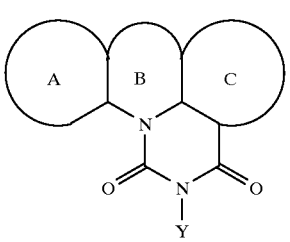

(I)

wherein ring A represents an optionally substituted monocyclic aromatic ring or a dicyclic fused ring in which at least one of the rings is an aromatic ring; the ring B represents pyrrole, 4H-1,4-oxazine, 4H-1,4-thiazine or 4(1H)-pyridone; and ring C represents an optionally substituted, monocyclic or dicyclic fused aromatic ring; and Y represents a group represented by the formula —e—f wherein e represents a lower alkylene; and f represents amidino, guanidino or amino, which can be optionally substituted with a lower alkyl which can be hydroxylated or lower-alkylaminated;

provided that the cases where the rings A and C are both optionally substituted monocyclic aromatic rings are excluded.

2. The compound as set forth in claim 1 wherein the ring A is a naphthalene, indene, benzocycloheptene or benzocyclooctene which is optionally substituted and optionally hydrogenated in one ring, or pharmacologically acceptable salts thereof.

3. The compound as set forth in claim 1 wherein the ring A is a quinoline, isoquinoline, 4H-1-benzopyran, 1H-2-benzopyran, 1,3-benzodioxole, benzofuran, isobenzofuran, benzothiophene, indole or isoindole which is optionally substituted and optionally hydrogenated in one ring and fused to the ring B at the benzene ring moiety thereof, or pharmacologically acceptable salts thereof.

4. The compound as set forth in claim 1 wherein the ring A is an optionally substituted tetralin or indan and fused to the ring B at the benzene ring moiety thereof, or pharmacologically acceptable salts thereof.

5. The compound as set forth in claim 1 wherein the ring A is an oxo-substituted tetralin or indan and fused to the ring B at the benzene ring moiety thereof, or pharmacologically acceptable salts thereof.

6. The compound as set forth in claim 1 wherein the ring A is an optionally substituted chroman, isochroman, tetrahydrobenzofuran or tetrahydroisobenzofuran and fused to the ring B at the benzene ring moiety thereof, or pharmacologically acceptable salts thereof.

7. The compound as set forth in claim 1 wherein the ring B is a pyrrole, or pharmacologically acceptable salts thereof.

8. The compound as set forth in claim 1 wherein the ring C is an optionally substituted benzene, or pharmacologically acceptable salts thereof.

9. The compound as claimed in claim 1 wherein f in the definition of Y is a lower alkyl-substituted amino, or pharmacologically acceptable salts thereof.

10. A process for producing a compound as set forth in claim 1 or pharmacologically acceptable salts thereof characterized by reacting a compound represented by the following general formula (II):

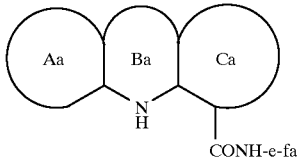

(II)

wherein the rings Aa and Ca respectively represent an optionally protected rings A and C as described in claim 1; the ring Ba represents a pyrrole, 4H-1,4-oxazine, 4H-1,4-thiazine or 4(1H)-pyridone; fa represents an optionally protected f as described in claim 1; and e has the same meaning as defined in claim 1, with a compound represented by the following general formula (III):

(III)

wherein D and E are the same or different and each represents a leaving group, and eliminating the protecting group(s), if any, from the product thus obtained.

11. A medicinal composition comprising a pharmacologically efficacious dose of the fused polycyclic heterocycle derivative as claimed in claim 1 or pharmacologically acceptable salts thereof and pharmacologically acceptable carriers.

12. A method for treating tumors which comprises administering the fused polycyclic heterocycle derivative as claimed in claim 1 in an effective antitumor amount to a patient in need thereof.

* * * * *